United States Patent
David et al.

(10) Patent No.: US 10,654,807 B2
(45) Date of Patent: May 19, 2020

(54) TOLL-LIKE RECEPTOR 8 AGONISTS

(71) Applicant: The University Of Kansas, Lawrence, KS (US)

(72) Inventors: Sunil Abraham David, St. Paul, MS (US); Hari Prasad Kokatla, Telangana (IN); Diptesh Sil, Gujarat (IN); Subbalakshmi Malladi, Lawrence, KS (US); Lauren Miranda Fox, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 65 days.

(21) Appl. No.: 15/106,488

(22) PCT Filed: Dec. 19, 2014

(86) PCT No.: PCT/US2014/071641
§ 371 (c)(1),
(2) Date: Jun. 20, 2016

(87) PCT Pub. No.: WO2015/095780
PCT Pub. Date: Jun. 25, 2015

(65) Prior Publication Data
US 2016/0347715 A1 Dec. 1, 2016

Related U.S. Application Data

(60) Provisional application No. 61/919,253, filed on Dec. 20, 2013, provisional application No. 62/022,918, filed on Jul. 10, 2014.

(51) Int. Cl.
| | |
|---|---|
| *C07D 215/38* | (2006.01) |
| *A61K 31/47* | (2006.01) |
| *A61K 39/39* | (2006.01) |
| *A61K 39/00* | (2006.01) |

(52) U.S. Cl.
CPC ............ *C07D 215/38* (2013.01); *A61K 31/47* (2013.01); *A61K 39/39* (2013.01); *A61K 2039/55* (2013.01); *A61K 2039/55511* (2013.01); *A61K 2039/57* (2013.01)

(58) Field of Classification Search
CPC .................................................. C07D 215/38
See application file for complete search history.

(56) References Cited

U.S. PATENT DOCUMENTS

| | | | | |
|---|---|---|---|---|
| 4,985,439 | A * | 1/1991 | Hwang | B01D 15/08 514/312 |
| 8,686,002 | B2 * | 4/2014 | Amberg | C07D 215/38 514/313 |
| 2006/0183909 | A1 | 8/2006 | Schmitt et al. | |
| 2008/0267986 | A1 * | 10/2008 | Pfeifer | A61K 39/0008 424/185.1 |
| 2010/0113565 | A1 | 5/2010 | Gorden et al. | |
| 2012/0294885 | A1 | 11/2012 | David et al. | |

OTHER PUBLICATIONS

Garanti et al. ("Thermochemical Behavior of o-Azidocinnamonitriles" J. Org. Chem. 1980, 45, 4767-4769).*
Zhou et al. ("Low-Valent Titanium Induced Reductive Coupling of Nitriles with Nitro Compounds," Synthetic Communications, 1998, 28(17), 3249-3262).*
PubChem. Compound Summary for: CID 12595028. Create Date: Feb. 8, 2007. (retrieved on Apr. 10, 2015). Retrieved from the Internet. <URL: https://pubchem.ncbi.nlm.nih.gov/compound/12595028>.
PubChem. Compound Summary for: CID 21341991. Create Date: Dec. 15, 2007. (retrieved on Feb. 11, 2015). Retrieved from the Internet. <URL: https://pubchem.ncbi.nlm.nih.gov/compound/21341991>.

* cited by examiner

*Primary Examiner* — Yong S. Chong
(74) *Attorney, Agent, or Firm* — Maschoff Brennan; Jonathan M. Benns

(57) ABSTRACT

Compounds described herein can be used for therapeutic purposes. The compounds can be TLR agonists, such as TLR8 agonists. The compounds can be included in pharmaceutical compositions and used for therapies were being a TLR8 agonist is useful. The pharmaceutical compositions can include any ingredients, such as carries, diluents, excipients, fillers or the like that are common in pharmaceutical compositions. The compounds can be those illustrated or described herein as well as derivative thereof, prodrug thereof, salt thereof, or stereoisomer thereof, or having any chirality at any chiral center, or tautomer, polymorph, solvate, or combinations thereof. As such, the compounds can be used as adjuvants in vaccines as well as for other therapeutic purposes described herein. The compounds can have any one of the formulae described herein or derivative thereof.

16 Claims, 18 Drawing Sheets

TOLL-LIKE RECEPTOR 8 AGONISTS

CROSS-REFERENCE

This patent application claims benefit of U.S. Provisional Application Ser. No. 61/919,253 filed Dec. 20, 2013, and of U.S. Provisional Application Ser. No. 62/022,918 filed Jul. 10, 2014, which provisional applications are incorporated herein by specific reference in its entirety.

GOVERNMENT RIGHTS

This invention was made with government support under HHSN2722009000033C awarded by the National Institutes of Health and National Institute of Allergy and Infectious Diseases. The government has certain rights in the invention.

BACKGROUND

It has been found that host responses to pathogens can be mediated via highly coordinated mechanisms involving both innate and adaptive limbs of the immune system. The innate immune system utilizes germline-encoded pattern recognition receptors (PRRs) to detect pathogen-associated molecular patterns (PAMPs) that are distinct and unique to the pathogen. PRRs encompass a broad range of molecules that are secreted into the extracellular environment (e.g., collectins, ficolins, pentraxins, alarmins), exist in the cytosol (e.g., retinoic acid-inducible gene I-like receptors, and the nucleotide-binding domain and leucine-rich repeatcontaining receptors), or are present on membranes.

Important among the transmembrane PRRs are the Toll-like receptors (TLR5), which are either expressed on the plasma membrane or in the endolysosomal compartments. At least 10 functional TLRs are encoded in the human genome, each with an extracellular domain having leucine-rich repeats (LRR) and a cytosolic domain called the Toll/IL-1 receptor (TIR) domain. The ligands for these receptors are highly conserved microbial molecules such as lipopolysaccharides (LPS) (recognized by TLR4), lipopeptides (TLR2 in combination with TLR1 or TLR6), flagellin (TLR5), single stranded RNA (TLR7 and TLR8), double stranded RNA (TLR3), CpG motif-containing DNA (recognized by TLR9), and profilin present on uropathogenic bacteria (TLR11). TLR1, -2, -4, -5, and -6 recognize extracellular stimuli, while TLR3, -7, -8 and -9 function within the endolysosomal compartment. The activation of TLRs by their cognate ligands leads to production of inflammatory cytokines, and up-regulation of major histocompatibility complex (MHC) molecules and co-stimulatory signals in antigen-presenting cells as well as activating natural killer (NK) cells (innate immune response), which lead to the priming and amplification of T-, and B-cell effector functions (adaptive immune responses).

In many instances, a TLR agonist may agonize multiple TLRs. However, it may be advantageous to selectively target only one TLR, such as TLR8, for therapeutic, diagnostic, or other purposes.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

Figure 1:
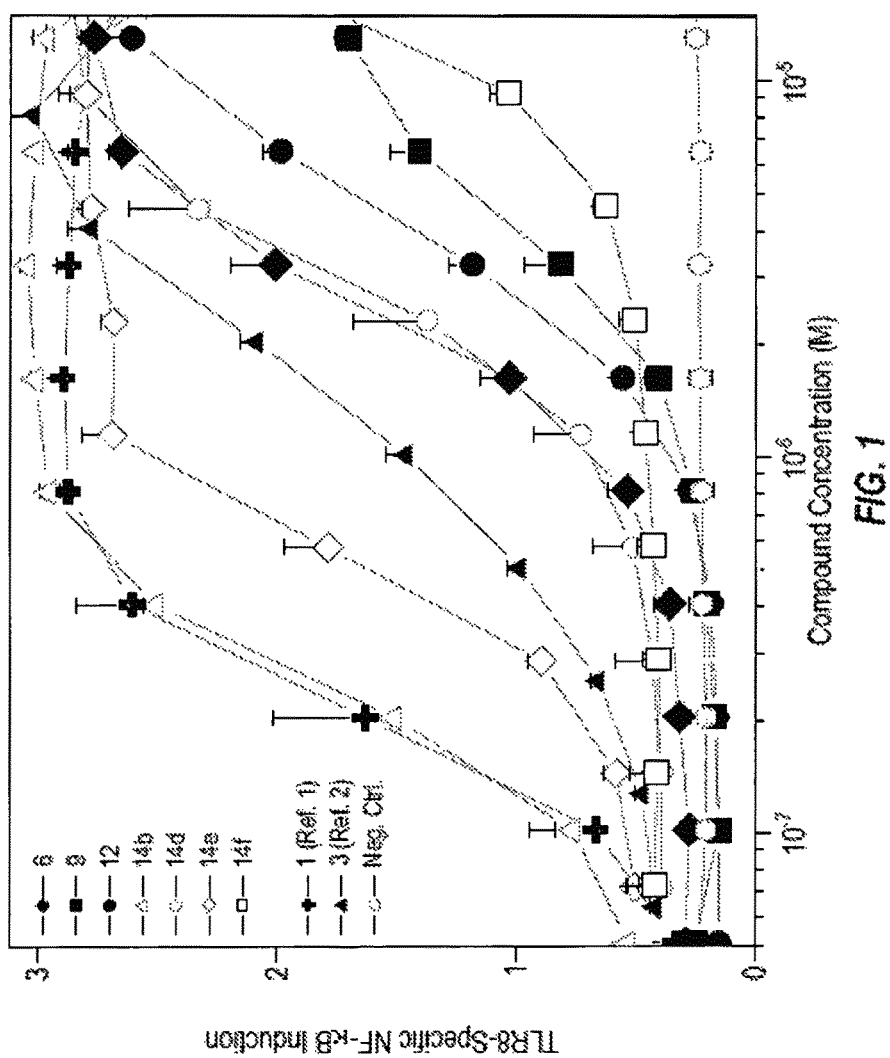
FIG. 1 includes a graph showing dose-response profiles of human TLR8 agonistic activities of 3-substituted 2-aminoquinolines, Compounds 1 and 3 were used as comparators FIG. 2 includes a graph that shows human TLR8-agonistic potency ($EC_{50}$ values) of a homologous series of 3-alkyl analogues (Compounds 6a-6e), showing maximal activity with a C3-butyl chain, and branched chain analogues (Compounds 6f-6i) are less potent.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to compounds described herein. The compounds can be TLR8 agonists that have specificity for TLR8 over other TLRs, such as for example specificity for TLR8 over TLR7. The compounds can be included in pharmaceutical compositions and used for therapies where being a TLR8 agonist is useful. The pharmaceutical compositions can include any ingredients, such as carries, diluents, excipients, fillers or the like that are common in pharmaceutical compositions. The compounds can be those illustrated or described herein as well as derivative thereof, prodrug thereof, salt thereof, or stereoisomer thereof, or having any chirality at any chiral center, or tautomer, polymorph, solvate, or combinations thereof.

Toll-like receptor (TLR)-8 agonists described herein can activate adaptive immune responses by inducing robust production of T helper 1-polarizing cytokines, suggesting that TLR8-active compounds may be promising candidate adjuvants for neonatal vaccines. The TLR8 agonists can be substituted aminoquinolines, such as 3-substituted aminoquinolines or 4-substituted aminoquinoline or 3,4-di-substituted aminoquinolines, which can be separate substitutions or 3,4-ring forming substitution. A specific example is 3-pentyl-quinoline-2-amine or derivative or prodrug or salt thereof.

Also, the TLR8 agonists can be synthesized furo[2,3-c] quinolines and regioisomeric furo[3,2-c]quinolines, derived via a tandem, one-pot Sonogashira coupling and intramolecular 5 endo-dig cyclization strategy. A pure TLR8 agonistic activity profile was observed in select furo[2,3-c] quinolines, with maximal potency conferred by a C2-butyl group ($EC_{50}$: 1.6 µM); shorter, longer, or substituted homologues can also be useful. This compound displayed prominent proinflammatory cytokine induction (including interleukin-12 and interleukin-18), but was entirely bereft of Type I interferon-inducing properties, confirming its selectivity for human TLR8.

In one embodiment, a compound of the invention can include the structure of Formula 1 or Formula 2, derivative thereof, prodrug thereof, salt thereof, or stereoisomer thereof, or having any chirality at any chiral center, or tautomer, polymorph, solvate, or combinations thereof.

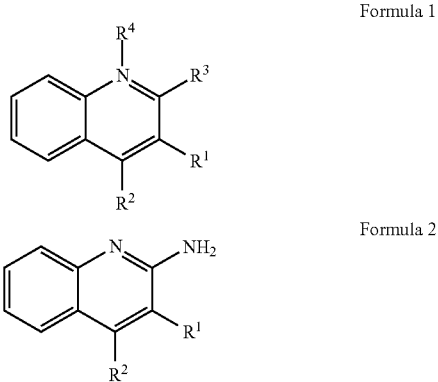

Formula 1

Formula 2

In Formula 1 or Formula 2 the variables can have the following values: $R^1$ and $R^2$ are each independently selected from (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(NR$^{1b}$R$^{1c}$)R$^{1a}$, —C(O)CH(N(R$^{1c}$)C(O)R$^{1b}$)R$^{1a}$, —C(O)CH(N(R$^{1c}$)C(O)OR$^{1b}$)R$^{1a}$, C(O)CH(N(R$^{1c}$)C(O)NR$^{1b}$R$^{1d}$)R$^{1a}$, C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$; (d) two adjacent R groups (e.g., $R^1$ and $R^2$) form a cyclic group, such as an aryl, heteroaryl, polyaryl, polyheteroaryl, or cycloalkyl or cycloheteroaryl, or furyl with the furyl oxygen off the carbon linked to $R^1$ or $R^2$; or (e) $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO— alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—S$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$); (f) derivatives thereof; and (g) combinations thereof. Wherein each R group (e.g., $R^1$ or $R^2$) is optionally substituted by a substituent Q, which substituent Q is defined as $R^1$. Wherein each R group variable is optionally —NHR, such that $R^1$ is —NHR$^{a1}$, $R^2$ is —NHR$^{a2}$, $R^3$ is —NHR$^{a3}$, $R^4$ is —NHR$^{a4}$, $R^5$ is —NHR$^{a5}$, $R^6$ is —NHR$^{a6}$, and $R^7$ is —NHR$^{a7}$. Wherein $R^{a1}$, $R^{a2}$, $R^{a3}$, $R^{a4}$, $R^{a5}$, $R^{a6}$, $R^{a7}$, $R^{1a}$, $R^{1b}$, $R^{1c}$, or $R^{1d}$ are each independently as defined for $R^1$, such as the selections (a), (b), (d), (e), (f), and (g). In one option, $R^{1a}$, $R^{1b}$, $R^{1c}$, or $R^{1d}$ are not the selection (c) that recites variables of $R^{a7}$, $R^{1a}$, $R^{1b}$, $R^{1c}$, or $R^{1d}$, or the variable iteration can be 1, 2, or 3 iterations of $R^{a7}$, $R^{1a}$, $R^{1b}$, $R^{1c}$, or $R^{1d}$ variables to a definite value. Each hetero, such as heteroaryl or heteroalkyl (e.g., alkyl with hetero atoms and carbon atoms), can include a backbone atom being other can C, such as being Si, N, O, P, or S. Each alkyl can be $C_1$-$C_{12}$ alkyl, $C_1$-$C_8$ alkyl, or $C_1$-$C_6$ alkyl. Each alkenyl can be $C_2$-$C_{12}$ alkenyl, $C_2$-$C_8$ alkenyl, or $C_2$-$C_6$ alkenyl. Each alkynyl can be $C_2$-$C_{12}$ alkynyl, $C_2$-$C_8$ alkynyl, or $C_2$-$C_6$ alkynyl. Each aryl can be monoaryl or polyaryl and can be $C_5$-$C_P$ aryl, wherein P can be any integer that results in being aromatic. Each polyaryl or polycycle can be 5,5-fused, 5,6-fused, or 6,6 fused with homo or hetero backbone, such as homoarylene or heteroarylene. In Formula 1 the $R^3$ can be hydrogen or NH$_2$. In Formula 1 the $R^4$ can be nothing or a negatively charged ion or atom that associates or bonds with the positively charged nitrogen to which it is linked, where an example of a negatively charged atom can be oxygen. In one option, when $R^3$ is $NH_2$, then $R^4$ is nothing, or when $R^4$ is O then $R^3$ is H. Specific examples of R group variables and examples of compounds formed therefrom are included herein as examples.

In one embodiment, for any of the formulae $R^2$ is hydrogen and $R^1$ is as defined herein, or shown to part of a compound that is a TLR8 agonist.

In one embodiment, when $R^1$ and $R^2$ form a ring, it is a furo ring with the furyl with the furyl oxygen off the carbon linked to $R^1$ or $R^2$. When $R^1$ and $R^2$ form a furo ring the other carbon atoms of the ring may be substituted with R groups, which can independently be the same as defined for $R^1$.

In one embodiment, the compound has the structure of Formula 2, derivative thereof, prodrug thereof, salt thereof, or stereoisomer thereof, or having any chirality at any chiral center, or tautomer, polymorph, solvate, or combinations thereof with $R^1$ and $R^2$ as defined.

In one embodiment, a compound of the invention can include the structure of Formula 1A or Formula 2A, derivative thereof, prodrug thereof, salt thereof, or stereoisomer thereof, or having any chirality at any chiral center, or tautomer, polymorph, solvate, or combinations thereof, wherein $X^1$ and $X^2$ are individually C, O, N, or S, and $R^1$, $R^2$, $R^3$ and $R^4$ are as defined with the caveat that $R^1$ and $R^2$ do not cooperate to form a ring. In one aspect, $X^2$ is hydrogen and $R^2$ is nothing.

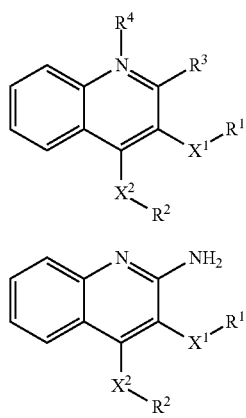

Formula 1A

Formula 2A

In one embodiment, a compound of the invention can include the structure of Formula 3 or Formula 4, derivative thereof, prodrug thereof, salt thereof, or stereoisomer thereof, or having any chirality at any chiral center, or tautomer, polymorph, solvate, or combinations thereof.

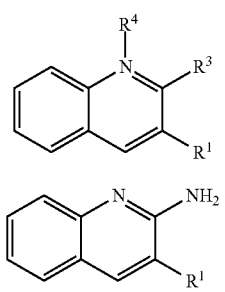

Formula 3

Formula 4

In Formula 3 or Formula 4 the variables can have the following values: $R^1$ can be selected from (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-13}$ aralkyl, heteroaryl, or heterocyclyl; or (c) —C(O)$R^{1a}$, —C(O)CH(NR$^{1b}$R$^{1c}$)R$^{1a}$, —C(O)CH(N(R$^{1c}$)C(O)R$^{1b}$)R$^{1a}$, —C(O)CH(N(R$^{1c}$)C(O)OR$^{1b}$)R$^{1a}$, C(O)CH(N(R$^{1c}$)C(O)NR$^{1b}$R$^{1d}$)R$^{1a}$, C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$; (d) $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—S$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$); (e) derivatives thereof; and (r) combinations thereof. Wherein each $R^1$ is optionally substituted by a substituent Q, which substituent Q is defined as $R^1$. Wherein each $R^1$ group variable is optionally —NHR, such that $R^1$ is —NHR$^{a1}$, $R^2$ is —NHR$^{a2}$, $R^3$ is —NHR$^{a3}$, $R^4$ is —NHR$^{a4}$, $R^5$ is —NHR$^{a5}$, $R^6$ is —NHR$^{a6}$, and $R^7$ is —NHR$^{a7}$. Wherein $R^{a1}$, $R^{a2}$, $R^{a3}$, $R^{a4}$, $R^{a5}$, $R^{a6}$, $R^{a7}$, $R^{1a}$, $R^{1b}$, $R^{1c}$, or $R^{1d}$ are each independently as defined for $R^1$, such as the selections (a), (b), (d), (e), and (f). In one option, $R^{1a}$, $R^{1b}$, $R^{1c}$, or $R^{1d}$ are not the selection (c) that recites variables of $R^{a7}$, $R^{1a}$, $R^{1b}$, $R^{1c}$, or $R^{1d}$ or the variable iteration can be 1, 2, or 3 iterations of $R^{a7}$, $R^{1a}$, $R^{1b}$, $R^{1c}$, or $R^{1d}$ variables to a definite value. Each hetero, such as heteroaryl or heteroalkyl (e.g., alkyl with hetero atoms and carbon atoms), can include a backbone atom being other can C, such as being Si, N, O, P, or S. Each alkyl can be $C_1$-$C_{12}$ alkyl, $C_1$-$C_8$ alkyl, or $C_1$-$C_6$ alkyl. Each alkenyl can be $C_2$-$C_{12}$ alkenyl, $C_2$-$C_8$ alkenyl, or $C_2$-$C_6$ alkenyl. Each alkynyl can be $C_2$-$C_{12}$ alkynyl, $C_2$-$C_8$ alkynyl, or $C_2$-$C_6$ alkynyl. Each aryl can be monoaryl or polyaryl and can be $C_5$-$C_P$ aryl, wherein P can be any integer that results in being aromatic. Each polyaryl or polycycle can be 5,5-fused, 5,6-fused, or 6,6 fused with homo or hetero backbone, such as homoarylene or heteroarylene. In Formula 3 the $R^3$ can be hydrogen or $NH_2$. In Formula 3 the $R^4$ can be nothing or a negatively charged ion or atom that associates or bonds with the positively charged nitrogen to which it is linked, where an example of a negatively charged atom can be oxygen. In one option, when $R^3$ is $NH_2$, then $R^4$ is nothing, or when $R^4$ is O then $R^3$ is H.

In one embodiment, a compound of the invention can include the structure of Formula 3A or Formula 4A, derivative thereof, prodrug thereof, salt thereof, or stereoisomer thereof, or having any chirality at any chiral center, or tautomer, polymorph, solvate, or combinations thereof, wherein X is C, O, N, or S, and $R^1$, $R^3$, and $R^4$ are as defined.

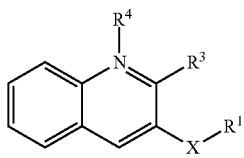

Formula 3A

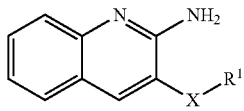

Formula 4A

In one embodiment, for the Formula 1, 1A, 2, 2A, 3, 3A, 4, and 4A, $R^1$ and/or $R^2$ can be $CH_3$, $C_2H_5$, $C_4H_9$, $C_5H_{11}$, $C_6H_{13}$, pent-1-en-1-yl, pent-4-en-1-yl, pent-1-yn-1-yl, methoxy, ethoxy, propoxy, butoxy, pentoxy, hexoxy, isopropyloxy, isobutyloxy, isopentyloxy, or 2-methylbutoxy. Alternatively, $R^2$ can be hydrogen with $R^1$ as defined.

In one embodiment, for Formula 3 or 3A or Formula 4 or 4A $R^1$ is not $C_6H_{13}$. In one aspect, $R^1$ is not $C_6H_{13}$ for any of the formulae.

In one embodiment, for any of the formulae $R^1$ and $R^2$ do not form a ring, and particularly do not form a furo ring.

In one embodiment, $R^1$ is one of $CH_3$, $C_2H_5$, $C_4H_9$, $C_5H_{11}$, pent-1-en-1-yl, pent-4-en-1-yl, pent-1-yn-1-yl, methoxy, ethoxy, propoxy, butoxy, pentoxy, hexoxy, isopropyloxy, isobutyloxy, isopentyloxy, or 2-methylbutoxy. In one aspect, X is O, or C. In one aspect, the compound is selected from one of Compounds 6, 9, 12, 14a, 14b, 14d, 14e, 14f, 61, 6b, 6c, 6d, 6e, 6f, 6g, 6h, and 6i. In one aspect, the compound is Compound 14b. In one aspect, the compound is not one of Compounds 14c, 21a, 21b, 21c, 24a, 24b, 27a, or 27b.

In one embodiment, for any of the formulae $R^1$ and $R^2$ cooperate to form a ring, and particularly form a furo ring.

In one embodiment, a compound of the invention can include the structure of Formula 5 or 5A or Formula 6 or 6A, derivative thereof, prodrug thereof, salt thereof, or stereoisomer thereof, or having any chirality at any chiral center, or tautomer, polymorph, solvate, or combinations thereof.

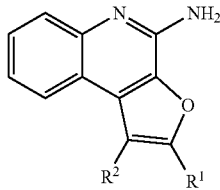

Formula 5

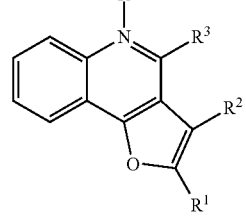

Formula 6

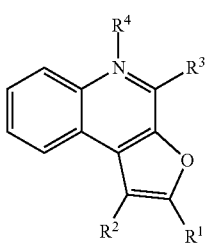

Formula 5A

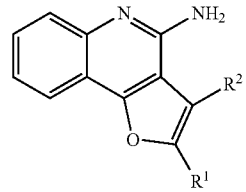

Formula 6A

In Formula 5 or 5A or Formula 6 or 6A the variables can have the following values: $R^1$ and $R^2$ can be independently selected from (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, C(O)CH(N($R^{1c}$)C(O)N$R^{1b}R^{1d}$)$R^{1a}$, C(O)OR$^{1a}$, —C(O)N$R^{1b}R^{1c}$, —C(N$R^{1a}$)N$R^{1b}R^{1c}$, —P(O)(O$R^{1a}$)$R^{1d}$, $CH_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$; (d) $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, alkaryl, etc.), nitro (—$NO_2$), nitroso (—NO), sulfo (—$SO_2$—OH), sulfonato (—$S_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$); (e) derivatives thereof; and (r) combinations thereof. Wherein each $R^1$ is optionally substituted by a substituent Q, which substituent Q is defined as $R^1$. Wherein each $R^1$ group variable is optionally —NHR, such that $R^1$ is —NHR$^{a1}$, $R^2$ is —NHR$^{a2}$, $R^3$ is —NHR$^{a3}$, $R^4$ is —NHR$^{a4}$, $R^5$ is —NHR$^{a5}$, $R^6$ is —NHR$^{a6}$, and $R^7$ is —NHR$^{a7}$. Wherein $R^{a1}$, $R^{a2}$, $R^{a3}$, $R^{a4}$, $R^{a5}$, $R^{a6}$, $R^{a7}$, $R^{1a}$, $R^{1b}$, $R^{1c}$, or $R^{1d}$ are each independently as defined for $R^1$, such as the selections (a), (b), (d), (e), and (f). In one option, $R^{1a}$, $R^{1b}$, $R^{1c}$, or $R^{1d}$ are not the selection (c) that recites variables of $R^{a7}$, $R^{1a}$, $R^{1b}$, $R^{1c}$, or $R^{1d}$, or the variable iteration can be 1, 2, or 3 iterations of $R^{a7}$, $R^{1a}$, $R^{1b}$, $R^{1c}$, or $R^{1d}$ variables to a definite value. Each hetero, such as heteroaryl or heteroalkyl (e.g., alkyl with hetero atoms and carbon atoms), can include a backbone atom being other can C, such as being Si, N, O, P, or S. Each alkyl can be $C_1$-$C_{12}$ alkyl, $C_1$-$C_8$ alkyl, or $C_1$-$C_6$ alkyl. Each alkenyl can be $C_2$-$C_{12}$ alkenyl, $C_2$-$C_8$ alkenyl, or $C_2$-$C_6$ alkenyl. Each alkynyl can be $C_2$-$C_{12}$ alkynyl, $C_2$-$C_8$ alkynyl, or $C_2$-$C_6$ alkynyl. Each aryl can be monoaryl or polyaryl and can be $C_5$-$C_P$ aryl, wherein P can be any integer that results in being aromatic. Each polyaryl or polycycle can be 5,5-fused, 5,6-fused, or 6,6 fused with homo or hetero backbone, such as homoarylene or heteroarylene. In Formula 5 or 5A the $R^3$ can be hydrogen or $NH_2$. In Formula 5 or 5A the $R^4$ can be nothing or a negatively charged ion or atom that associates or bonds with the positively charged nitrogen to which it is linked, where an example of a negatively charged atom can be oxygen. In one option in Formula 5 or 5A, when $R^3$ is $NH_2$, then $R^4$ is nothing, or when $R^4$ is O then $R^3$ is H.

In one embodiment for Formula 5 or 5A or Formula 6 or 6A, $R^2$ is hydrogen, and $R^1$ is $CH_3$, $C_2H_5$, $C_3H_7$, $C_4H_9$, $C_5H_{11}$, $C_6H_{13}$, $CH_2CH(CH_3)_2$, $C(CH_3)_3$, $C_2H_4CH(CH_3)_2$, cyclopropyl, cyclobutyl, cyclopentyl, cyclohexyl, methylcyclopropane, methylcyclobutane, methylcyclopentane, methylcyclohexane, benzyl, phenyl, alkylphenyl, $CH_2OH$, $C_2H_4OH$, $C_3H_6OH$, $C_4H_8OH$, 2-hydroxypropyl, 1-hydroxy-2-methylpropyl, propan-2-ol, ethoxyethyl, $CH_2NH_2$, or $C_2H_4NH_2$.

In one embodiment for Formula 5 or 5A or Formula 6 or 6A, $R^2$ is benzyl, and $R^1$ is H, $CH_3$, $C_2H_5$, $C_3H_7$, $C_4H_9$, $C_5H_{11}$, $C_6H_{13}$, $CH_2CH(CH_3)_2$, $C(CH_3)_3$, $C_2H_4CH(CH_3)_2$, cyclopropyl, cyclobutyl, cyclopentyl, cyclohexyl, methylcyclopropane, methylcyclobutane, methylcyclopentane, methylcyclohexane, benzyl, phenyl, alkylphenyl, $CH_2OH$, $C_2H_4OH$, $C_3H_6OH$, $C_4H_8OH$, 2-hydroxypropyl, 1-hydroxy-2-methylpropyl, propan-2-ol, ethoxyethyl, $CH_2NH_2$, or $C_2H_4NH_2$.

In one embodiment, $R^2$ is hydrogen or benzyl, and $R^1$ is one of $CH_3$, $C_2H_5$, $C_3H_7$, $C_4H_9$, $C_5H_{11}$, $C_6H_{13}$, $CH_2CH(CH_3)_2$, $C(CH_3)_3$, $C_2H_4CH(CH_3)_2$, cyclopropyl, cyclobutyl, cyclopentyl, cyclohexyl, methylcyclopropane, methylcyclobutane, methylcyclopentane, methylcyclohexane, benzyl, phenyl, alkylphenyl, $CH_2OH$, $C_2H_4OH$, $C_3H_6OH$, $C_4H_8OH$, 2-hydroxypropyl, 1-hydroxy-2-methylpropyl, propan-2-ol, ethoxyethyl, $CH_2NH_2$, or $C_2H_4NH_2$. In one aspect, $R^2$ is hydrogen. In one aspect, the compound is selected from one of Compounds A8b, A8c, A8d, A8e, A8f, A8g, A8h, or A8i. In one aspect, the compound is Compound A18d. In one aspect, the compound is not one of Compounds A8a, A8g, A8h, A8i, A8j, A8k, A8l, A8m, A8n, A8o, A8p, A8q, A8r, A8s, A8t, A8u A8v, A8w, A8x, A8y, A18, A21, or A24.

In certain embodiments, each R group of any of the formulae, particularly $R^1$ and/or $R^2$, are each independently selected from the recitations above or the following: 2(R)-(dimethylamino)propionyl, 2-(methoxycarbonylamino)propionyl, 2(R)-(methoxy-carbonylamino)propionyl, 2-(ethoxycarbonylamino)propionyl, 2(R)-(methoxycarbonyl-amino)-3-methoxy-propionyl, 2(R)-(methoxycarbonylamino)-3-aminocarbonyl-propionyl, 2-(methoxycarbonylamino)-2-methylpropionyl, 2(R)-(methoxycarbonylamino)-3(R)-hydroxy-butanoyl, 2(R)-(methoxycarbonylamino)-3 (S)-hydroxybutanoyl, 2(R)-(methoxycarbonyl-amino)-3-methylbutanoyl, 2(S)-(methoxycarbonylamino)-3-methylbutanoyl, 2(R)-(ethoxycarbonyl-amino)-3-methylbutanoyl, 2(S)-(ethoxycarbonylamino)-3-methylbutanoyl, 2(R)-(isoproxycarbonyl-amino)-3-methylbutanoyl, 2(S)-(isopropoxycarbonylamino)-3-methylbutanoyl, 2(R)-(tert-butoxycarbonylamino)-3-methylbutanoyl, 2(S)-(tert-butoxycarbonylamino)-3-methylbutanoyl, 2(R)-(methoxycarbonylamino)-3-hydroxy-3-methylbutanoyl, 2-(methoxycarbonylamino)-2-cyclopropyl-acetyl, 2-(methoxycarbonylamino)pentanoyl, 2-(methoxycarbonylamino)pent-4-enoyl, 1-(methoxycarbonylamino)cyclopropylcarbonyl, 1-(methoxycarbonylamino)-cyclobutylcarbonyl, 1-(methoxycarbonylamino)-cyclopentyl-carbonyl, 2(R)-(methoxycarbonylamino)-2-phenylacetyl, 2(R)-(ethoxycarbonylamino)-2-phenylacetyl, 2(R)-(isopropoxycarbonylamino)-2-phenylacetyl, 2(R)-(tert-butoxycarbonylamino)-2-phenylacetyl, 2(S)-(tert-butoxycarbonylamino)-2-phenylacetyl, 2(R)-(methoxycarbonyl-amino)-2-(2-chlorophenyl)acetyl, 2(R)-(dimethylamino)-2-phenylacetyl, 2-(dimethylamino)-2-(4-nitrophenyl)acetyl, 2-(dimethylamino)-2-(2-fluorophenyl) acetyl, 2(R)-(dimethylamino)-2-(2-fluorophenyl)acetyl, 2(S)-(dimethylamino)-2-(2-fluorophenyl)acetyl, 2-(dimethyl-amino)-2-(3-fluorophenyl)acetyl, 2-(dimethylamino)-2-(2-chlorophenyl)acetyl, 2(R)-(dimethylamino)-2-(2-chlorophenyl)acetyl, 2-(dimethylamino)-2-(3-chlorophenyl) acetyl, 2-(dimethylamino)-2-(4-chlorophenyl)acetyl, 2-(dimethylamino)-2-(2-trifluoromethyl-phenyl)acetyl, 2-(dimethyl-amino)-2-(3-trifluoromethylphenyl)acetyl, 2-(dimethylamino)-2-(thien-2-yl)acetyl, 2-(dimethyl-amino)-2-(thien-3-yl)acetyl, 2-(dimethylamino)-2-(2-methylthiazol-4-yl)acetyl, 2-(dimethylamino)-2-(benzothien-3-yl)acetyl, 2-(dimethylamino)-2-(2-methyl-benzothiazol-5-yl)acetyl, 2-(dimethylamino)-2-(benzoisoxazol-3-yl)acetyl, 2-(dimethylamino)-2-(quinolin-3-yl)acetyl, 2(R)-(diethylamino)-2-phenylacetyl, 2(R)-(methylethylamino)-2-phenylacetyl, 2-(dimethylamino)-2-naphth-1-ylacetyl, 2(R)-(pyrrolidin-1-yl)-2-phenylacetyl, 2-(3(S)-fluoropyrrolidin-1-yl)-2-phenylacetyl, 2(R)-(morpholin-4-yl)-2-phenylacetyl, 2(R)-(piperidin-1-yl)-2-phenylacetyl, 2(R)-(piperidin-1-yl)-2-(2-fluorophenyl)acetyl, 2-(4-hydroxy-piperidin-1-yl)-2-phenylacetyl, 2-(4-phenylpiperidin-1-yl)-2-phenylacetyl, 2(R)-(4-hydroxy-4-methylpiperidin-1-yl)-2-phenylacetyl, 2(R)-(4-hydroxy-4-phenylpiperidin-1-yl)-2-phenylacetyl, 2-(3-oxopiperazin-1-yl)-2-phenylacetyl, 2-(4-methylpiperazin-1-yl)-2-phenylacetyl, 2-(dimethylamino)-2-(pyridin-2-yl)acetyl, 2-(dimethylamino)-2-(pyridin-3-yl)acetyl, 2-(dimethylamino)-2-(pyridin-4-yl)acetyl, 2-(dimethylamino)-2-(6-chloropyridin-3-yl)acetyl, 2-(2-dimethylaminomethyl) phenylacetyl, 2-(2-pyrrolin-1-ylmethyl)phenylacetyl, 2-(2-piperidin-1-ylmethyl)phenylacetyl, 2-(2-morpholin-4-ylmethyl)phenylacetyl, 2-(2-(4-methylpiperazin-1-ylmethyl)phenylacetyl, 1-methylpyrrolidine-2(R)-carbonyl, 1-methyl-4(R)-fluoro-pyrrolidine-2(R)-carbonyl, 2-(R)-(methylaminoarbonylamino)-2-phenylacetyl, 2-(R)-(ethylaminoarbonylamino)-2-phenylacetyl, 2(R)-(cyclopentylaminoarbonylamino)-2-phenylacetyl, 2(R)-(dimethylaminoarbonylamino)-2-phenylacetyl, (N,N-benzylmethyl-amino)acetyl, and 2-(N,N-benzylmethylamino)-3-methylbutanoyl.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

The compounds can be toll-like receptor (TLR)-8 agonists that strongly induce the production of T helper 1-polarizing cytokines, and may therefore serve as vaccine adjuvants, especially for the very young and the elderly.

Pharmaceutical Compositions

Provided herein are pharmaceutical compositions comprising a compound provided herein as an active ingredient, including a single enantiomer, a racemic mixture, a mixture of diastereomers, or an isotopic variant thereof; or a pharmaceutically acceptable salt, solvate, or prodrug thereof; or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compounds provided herein may be administered alone, or in combination with one or more other compounds provided herein. The pharmaceutical compositions that comprise a compound provided herein including a single enantiomer, a racemic mixture, a mixture of diastereomers, or an isotopic variant thereof; or a pharmaceutically acceptable salt, solvate, or prodrug thereof, can be formulated in various dosage forms for oral, parenteral, intravenous, intramuscular, subcutaneous, and topical administration or the like. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

The pharmaceutical compositions provided herein can be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002. Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, cthanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound that is readily convertible into the parent compound in vivo. Prodrugs are often useful because, in some situations, they may be easier to administer than the parent compound. For example $R^1$ or $R^2$ may include a prodrug moiety that is cleaved in vivo to result in a functional compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977.

In one embodiment, a pharmaceutical composition can include a compound and a pharmaceutically acceptable carrier. In one aspect, the composition is configured for oral administration, parenteral administration, intravenous administration, topical administration, or subcutaneous administration. In one aspect, the compound is present in an amount sufficient for agonizing a Toll-Like Receptor (TLR), such as TLR8, and may be specific for only TLR8. In one aspect, the composition is a vaccine and includes a vaccine agent. The vaccine agent is the entity to which the vaccine provides for immunogenicity thereto.

In one embodiment, a method of agonizing a Toll-Like Receptor 8 (TLR8) can include providing a compound of one of the embodiments to a TLR8 in an amount sufficient to agonize the TLR8. The TLR8 can be in vitro or in vivo.

In one embodiment, a method of improving vaccination can include administering a vaccine agent (e.g., having an antigen) to a subject along with a compound of one the embodiments in an amount sufficient to function as an adjuvant with regard to the vaccine agent. The compound can be any compound provided herein or derivative thereof. The improved vaccination method can include agonizing a Toll-Like Receptor 8 (TLR8) in the subject. In one aspect, the method can include agonizing the TLR8 so as to increase production of inflammatory cytokines. In one aspect, the method can include agonizing the TLR8 so as to up-regulate major histocompatibility complex (MHC) molecules and co-stimulatory signals in antigen-presenting cells. In one aspect, the method can include agonizing the TLR8 so as to activate natural killer (NK) cells. In one aspect, the method can include agonizing the TLR8 so as to cause an adaptive immune response to the vaccine agent. In one aspect, the method can include agonizing the TLR8 so as to induce production of T helper 1-polarizing cytokines.

In one aspect, the subject is a youth under 10, 5, 4, 3, 2, or 1 years of age or a newborn younger than 12 months, 6 months, 4 months, 3 months, 2 months, or 1 month.

In one aspect, the subject is elderly, and the subject is elderly above 50, 60, or 70 years of age.

In one aspect, the compound is an agonist that is active for TLR8 and inactive to TLR7.

In one embodiment, a method of activating an immune system can include administering an immunological agent to a subject along with a compound of one of the embodiments in an amount sufficient to function as an adjuvant with regard to the immunological agent.

In one embodiment, a method of treating allergic bronchitis can include administering to a subject a compound of one of the embodiments. In one aspect, the subject has allergic bronchitis and is in need of treatment.

In one aspect, the subject of a method is in need of a therapy, such as vaccination or treatment.

In one embodiment, a method of treating bronchospastic disorder can include administering to a subject a compound of one of the embodiments. In one aspect, the subject has bronchospastic disorder and is in need of treatment.

In one embodiment, the compounds can be used as treatments for hepatitis, such as hepatitis C.

In one embodiment, methods of treating bronchial asthma and atopic bronchitis can include administering the TLR8 agonists.

In one embodiment, a method of activating a cytotoxic T lymph response can include administering a TLR8 agonist.

In one embodiment, the compounds can be TLR8 agonists that activate adaptive immune responses by inducing robust production of T helper 1-polarizing cytokines, suggesting that TLR8-active compounds may be promising candidate adjuvants. For example, there is pure TLR8 agonistic activity in a C2-butyl furo[2,3-c]quinoline.

Focused structure-based ligand design studies led to the identification of 3-pentyl-quinoline-2-amine as a novel, structurally simple, and highly potent human TLR8-specific agonist. Other 3- and 4-substituted aminoquinolines also had activity.

In one embodiment, the compounds are small molecule agonists of TLR8 and useful as potential vaccine adjuvants. The compounds can target TLR8 that is expressed in myeloid dendritic cells, monocytes, and monocyte-derived dendritic cells. Engagement by the TLR8 agonists can evoke a dominant proinflammatory cytokine profile including tumor necrosis factor-α (TNF-α), interleukin-12 (IL-12), and IL-18, and appear unique in markedly upregulating the production of Th1-polarizing cytokines TNF-α and IL-12 in neonatal antigen presenting cells. These data, taken together, suggest that the TLR8 agonists may be useful as adjuvants for enhancing immune responses in newborns.

Certain imidazoquinolines such as CL097 (Compound 2), and thiazoloquinolines such as CL075 (Compound 1), and the 2-aminobenzazepine VTX-2337 display mixed TLR7/TLR8-agonism, which may not be desirable. TLR8-biased agonistic properties have been described for a novel 2-aminobenzazepine derivative (VTX-294), whose complete structure has not been disclosed. A compound with pure TLR8 agonistic activity is a C2-butyl furo[2,3-c]quinoline (Compound 3) with IL-12 and IL-18 induction profiles, and yet without IFN-α inducing properties, confirming its selectivity for human TLR8. Crystal structures of the ectodomain of human TLR8 complexed with mixed TLR7/TLR8-agonistic thiazoloquinolines and imidazoquinolines (including Compound 1 and Compound 2) had allowed a rationalization of experimentally-determined SAR via induced-fit docking techniques.

The thiazoloquinoline Compound 1 as well as the furoquinoline Compound 3 were predicted to occupy the same binding pocket formed by both the TLR8 protomers with the binding geometry of the ligands and interacting residues being virtually identical; ionic H-bonds were observed between the C4-amine of both Compound 1 and Compound 3 with the sidechain carboxylate of Asp543 of TLR8, with additional stabilization derived from an H-bond between the β-OH group of Thr574 and either the $N^2$ atom of the thiazole ring of Compound 1 or the oxygen atom of the furanyl ring of Compound 3. Key π-π interactions of the quinoline moieties of Compound 1 and Compound 3 (Phe405/Tyr353), as well as hydrophobic interactions of the C2-alkyl group (Phe346/Ile403/Tyr348) were also observed to occur.

A high-resolution (1.8 Å) structure of human TLR8 co-crystallized with Compound 3 was obtained. An examination of the complex confirmed similar binding geometries of Compound 2 and Compound 3. The occupancy of TLR8 with Compound 3 induced, as expected, a significant reorganization to form the binding pocket, reflected in significant Cα deviations corresponding primarily to loops of leucine-rich repeats (LRRs). However, the occupancy of Compound 3 in TLR8 is associated with greater excursions of LRR8 and, particularly, of residues 572-574 in LRR18 such that predicted H-bond between Thr574 and the oxygen atom of the furanyl ring of Compound 3 is lost in the crystal structure of the complex. Accordingly, the furan ring in Compound 3 is optional, and thereby simple 3- and 4-substituted aminoquinolines were determined via classic disconnection strategies.

Initially, a 3-alkoxy-2-aminoquinoline series was derived by disconnection at C1 in Compound 3. The 3-butoxy analogue Compound 6 was synthesized from commercially-available 3-hydroxy quinoline via O-alkylation and installation of the amine at C2 using Scheme 1.

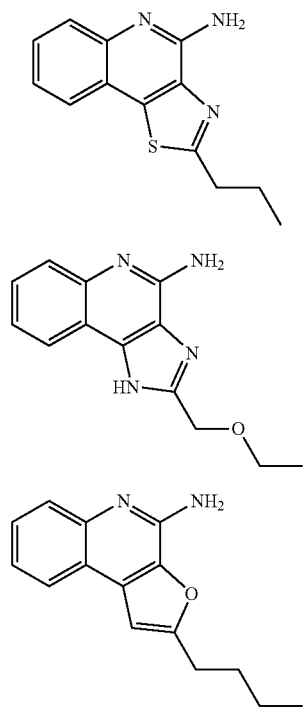

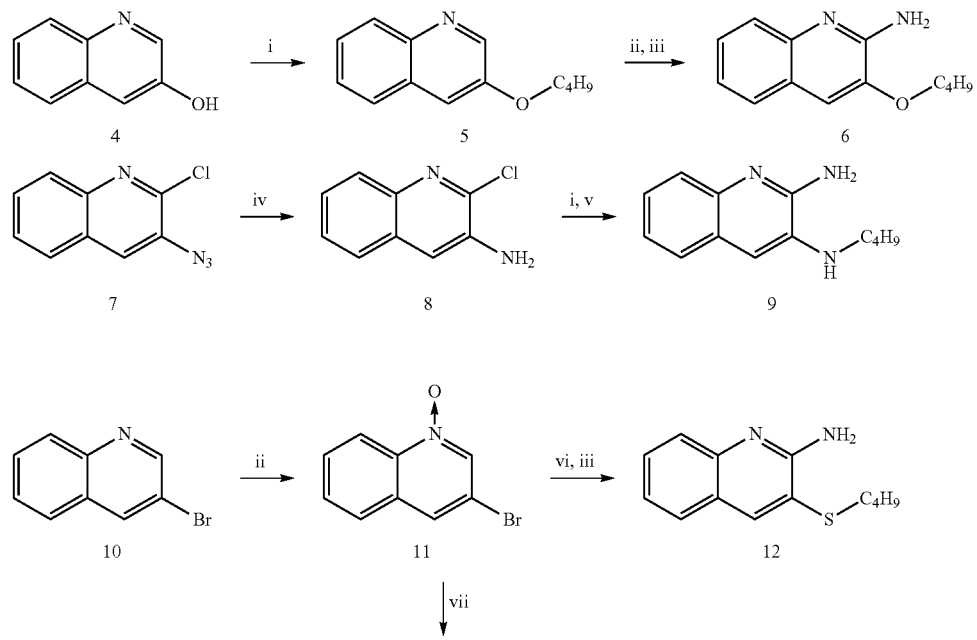

Scheme 1

-continued

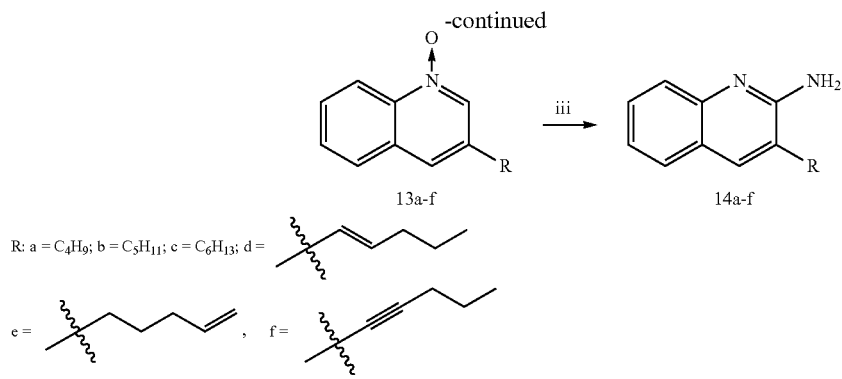

R: a = C$_4$H$_9$; b = C$_5$H$_{11}$; c = C$_6$H$_{13}$; d = [structure]; e = [structure], f = [structure]

Scheme 1 shows the syntheses of 3-substituted quinolin-2-amine analogues. Reagents: (i) butyl iodide, K$_2$CO$_3$, DMSO; (ii) m-CPBA, CHCl$_3$; (iii) (a) benzoyl isocyanate, CH$_2$Cl$_2$; (b) NaOMe, MeOH; (iv) H$_2$, Pt/C, EtOH; (v) NH$_3$, MeOH; (vi) butylSH, NaH, DMSO; (vii) Pd(PPh$_3$)$_4$, RB(OH)$_2$, K$_2$CO$_3$, 1,4-dioxane, for 14f: Pd(PPh$_3$)$_4$, CuI, 1-pentyne, Et$_3$N:CH$_3$CN (1:3).

A homologous series of compounds were also synthesized (Scheme S1).

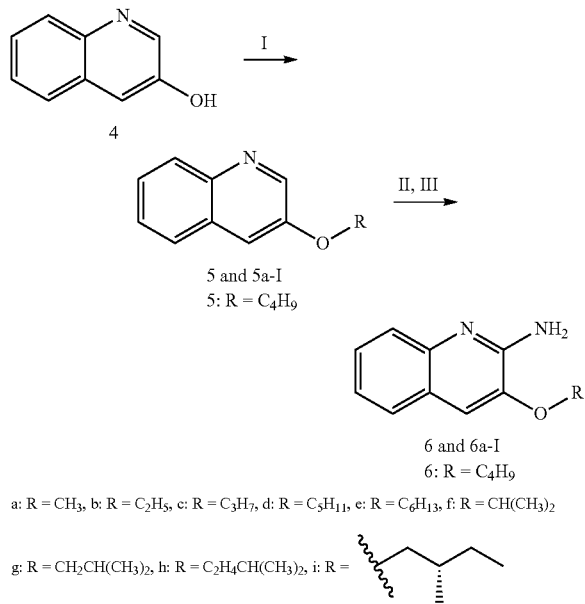

a: R = CH$_3$, b: R = C$_2$H$_5$, c: R = C$_3$H$_7$, d: R = C$_5$H$_{11}$, e: R = C$_6$H$_{13}$, f: R = CH(CH$_3$)$_2$ g: R = CH$_2$CH(CH$_3$)$_2$, h: R = C$_2$H$_4$CH(CH$_3$)$_2$, i: R = [structure]

Scheme S1 shows syntheses of 3-alkoxyquinolin-2-amine analogues. Reagents: (i) RI, NaH, DMSO; (ii) m-CPBA, CHCl$_3$; (iii) (a) benzoyl isocyanate, CH$_2$Cl$_2$, (b) NaOMe, MeOH.

Figure 2:
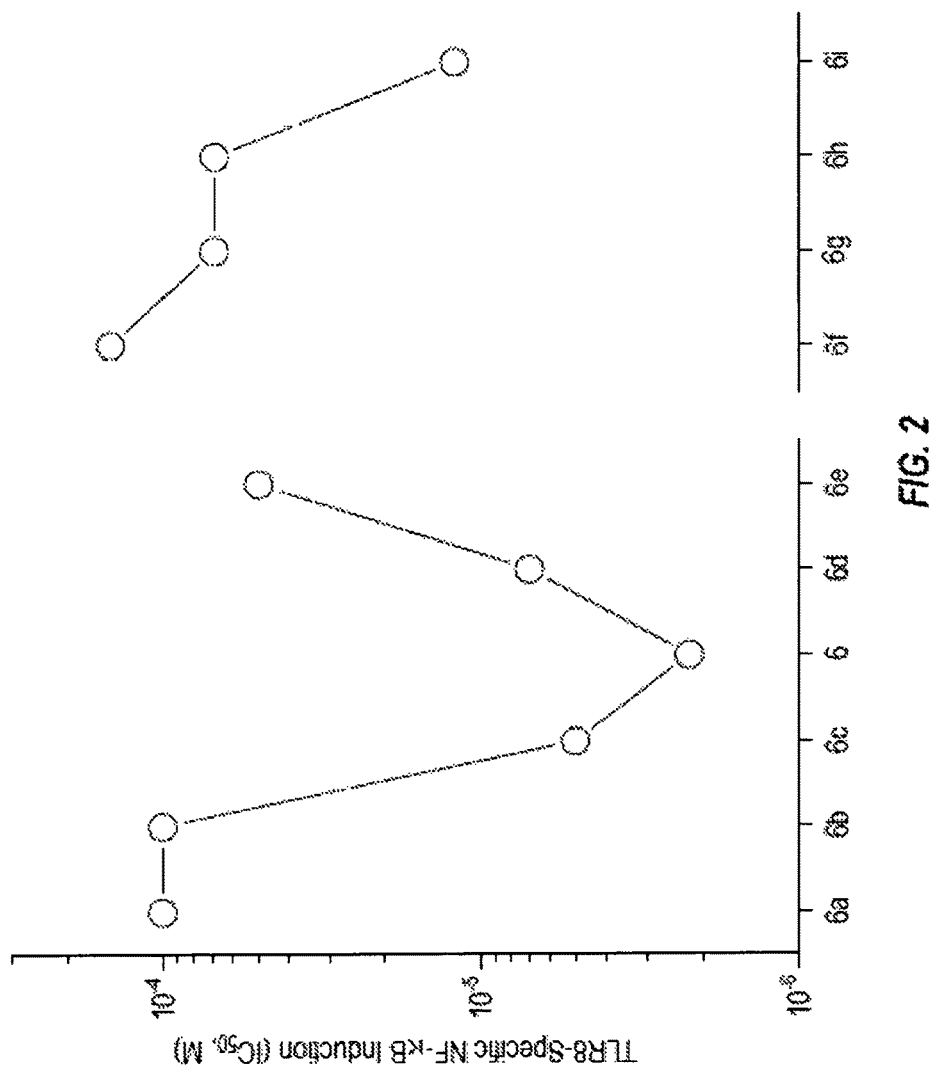

The homologous series showed a clear dependence of substituent chain length at C3 with the optimal analogue being Compound 6, which showed maximal agonistic potency in a cell-based TLR8-specific NF-κB transactivation assay (EC$_{50}$ of 2.2 μM; FIGS. 1 and 2, Table 1).

FIG. 1 shows dose-response profiles of human TLR8 agonistic activities of 3-substituted 2-aminoquinolines, where error bars represent standard deviations obtained on quadruplicates, and where Compounds 1 and 3 were used as comparators. FIG. 2 shows human TLR8-agonistic potency (EC$_{50}$ values) of a homologous series of 3-alkyl analogues (Compounds 6a-6e), showing maximal activity with a C3-butyl chain, and where branched chain analogues (Compounds 6f-6i) are less potent.

Synthetic chemistry was used to synthesize N$^3$-butylquinoline and 3-(butylthio)quinoline analogues (Compound 9 and Compound 12, respectively), as well as the 3-alkylquinolin-2-amines of Compounds 14a-f (see Scheme 1). Accessing the N$^3$-butylquinoline Compound 9 by conventional strategies via N-oxidation of the commercially available 3-aminoquinoline was problematic, and it was expedient to utilize as starting material 2-chloro-3-azidoquinoline Compound 7 (derived from commercially available 2-chloro-3-quinolineboronic acid). S-alkylation of 3-bromoquinoline 1-oxide obviated the problem of over-oxidation to the sulfone derivative (which was found to be completely inactive) in the synthesis of the 3-(butylthio)quinoline Compound 12.

A comparison of the activities of these analogues in TLR8 primary screens yielded a clear structure-activity relationship. The TLR8-agonistic potency of the 3-pentyl quinolone Compound 14b was 0.2 μM, i.e., ten-fold greater than that of the 3-butoxy analogue Compound 6b, eight times greater than that of the parent Compound 3 (EC$_{50}$: 1.6 μM), and rivaling that of the reference Compound 1 (FIG. 1), while the 3-(butylthio)quinoline and N$^3$-butylquinoline analogues were weaker (EC$_{50}$: 4.2 μM and 4.3 μM for Compounds 12 and 9, respectively; FIG. 1) but likely still useful.

As shown in Scheme 2, analogues that are Compounds 21a-c were synthesized starting from 3-iodoquinolin-4-ol (Compound 15).

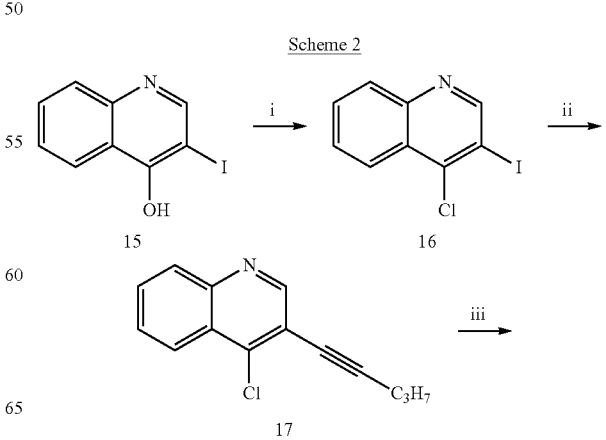

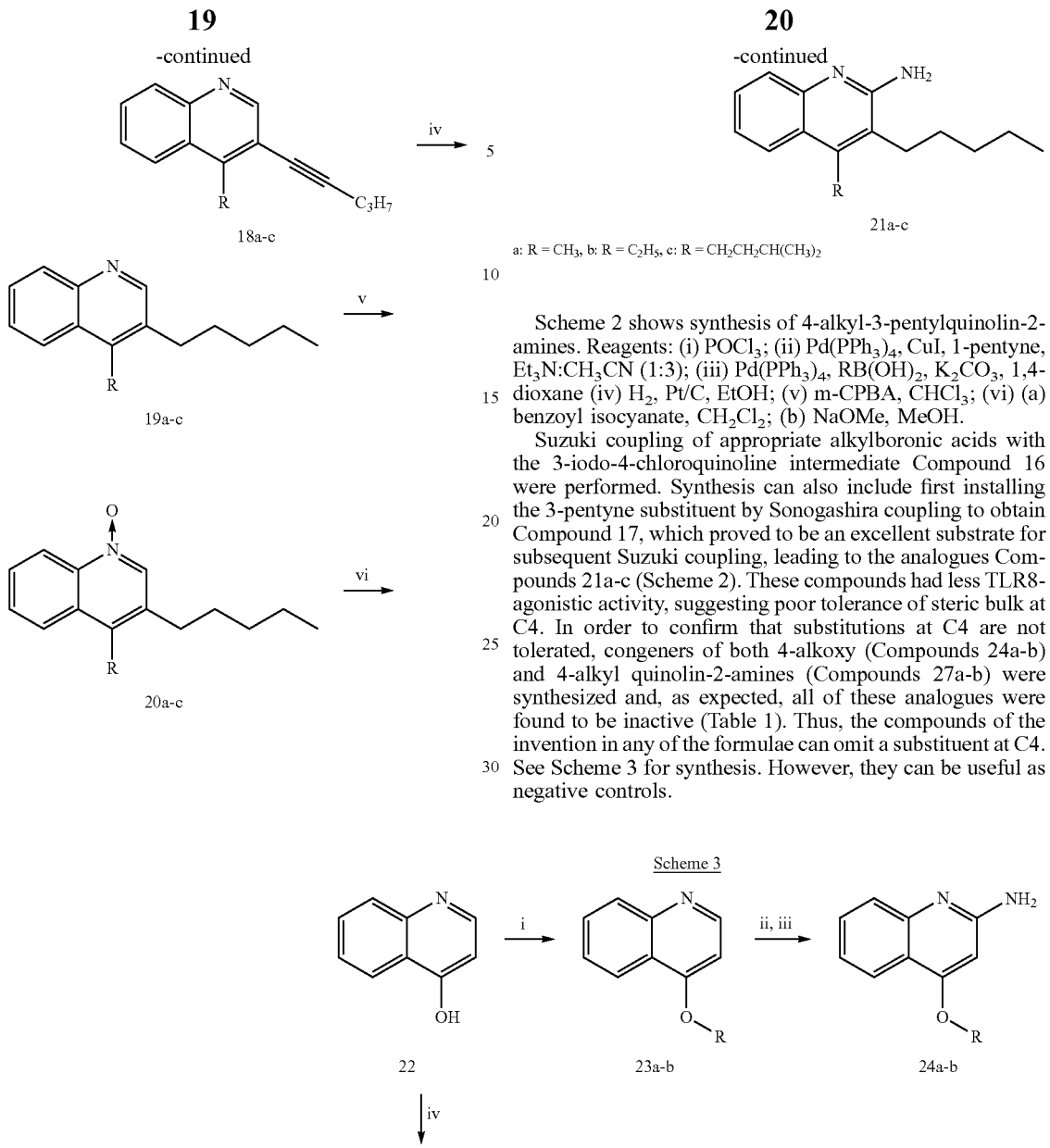

Scheme 2 shows synthesis of 4-alkyl-3-pentylquinolin-2-amines. Reagents: (i) POCl$_3$; (ii) Pd(PPh$_3$)$_4$, CuI, 1-pentyne, Et$_3$N:CH$_3$CN (1:3); (iii) Pd(PPh$_3$)$_4$, RB(OH)$_2$, K$_2$CO$_3$, 1,4-dioxane (iv) H$_2$, Pt/C, EtOH; (v) m-CPBA, CHCl$_3$; (vi) (a) benzoyl isocyanate, CH$_2$Cl$_2$; (b) NaOMe, MeOH.

Suzuki coupling of appropriate alkylboronic acids with the 3-iodo-4-chloroquinoline intermediate Compound 16 were performed. Synthesis can also include first installing the 3-pentyne substituent by Sonogashira coupling to obtain Compound 17, which proved to be an excellent substrate for subsequent Suzuki coupling, leading to the analogues Compounds 21a-c (Scheme 2). These compounds had less TLR8-agonistic activity, suggesting poor tolerance of steric bulk at C4. In order to confirm that substitutions at C4 are not tolerated, congeners of both 4-alkoxy (Compounds 24a-b) and 4-alkyl quinolin-2-amines (Compounds 27a-b) were synthesized and, as expected, all of these analogues were found to be inactive (Table 1). Thus, the compounds of the invention in any of the formulae can omit a substituent at C4. See Scheme 3 for synthesis. However, they can be useful as negative controls.

Scheme 3 shows synthesis of 4-substituted quinolin-2-amines. Reagents: (i) butyl iodide, NaH, DMSO; (ii) m-CPBA, CHCl$_3$; (iii) (a) benzoyl isocyanate, CH$_2$Cl$_2$; (b) NaOMe, MeOH; (iv) POCl$_3$; (v) Pd(PPh$_3$)$_4$, RB(OH)$_2$, K$_2$CO$_3$, 1,4-dioxane.

All analogues were counter-screened in reporter cell lines specific for human TLR2, TLR3, TLR4, TLR5, TLR7, TLR9, TLR10, Nod1 and Nod2, and Compounds 6, 9, 12, and 14a-f were confirmed to be specific for human TLR8. The most potent analogue Compound 14b was characterized further in cytokine/chemokine induction profiles in a panel of secondary screens employing human peripheral blood mononuclear cells as well as whole human blood. Consistent with its specificity for TLR8, we observed the induction of a specific set of chemokines and proinflammatory cytokines, including interleukins 12 and 18 (FIGS. 3A-3T).

Figure 3A:
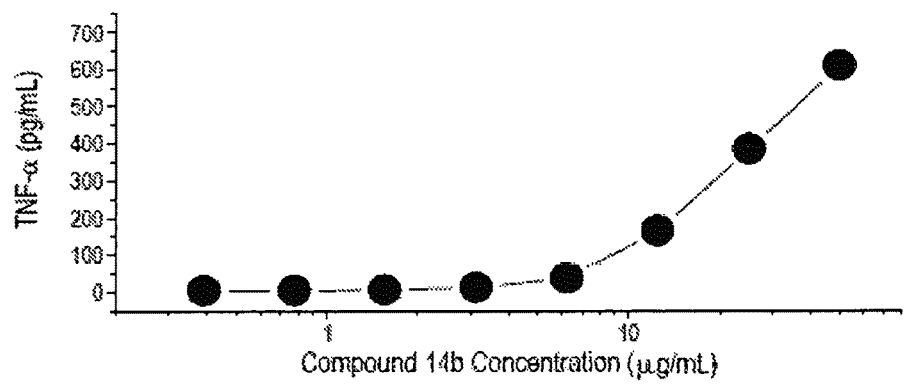
FIGS. 3A-3T include graphs that show induction of cytokines (FIG. 3A-3J) and chemokines (FIG. 3K-3T) in human PBMCs by the lead Compound 14b.
Figure 3B:
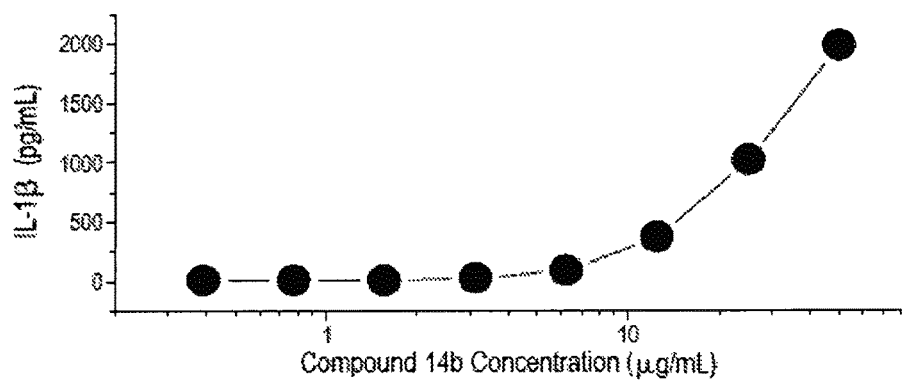
Figure 3C:
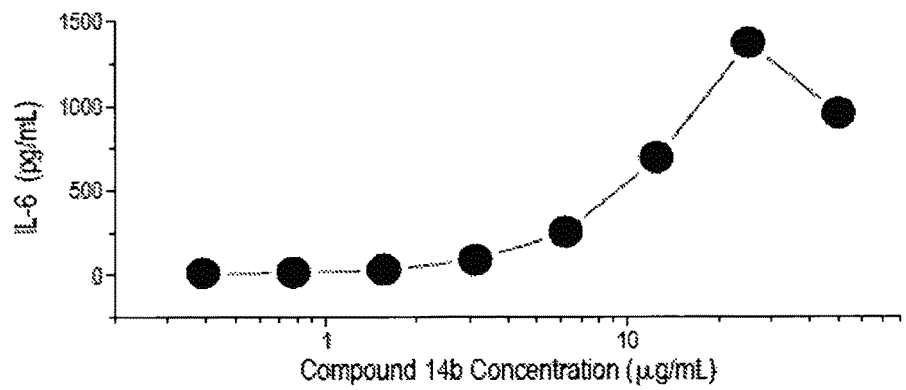
Figure 3D:
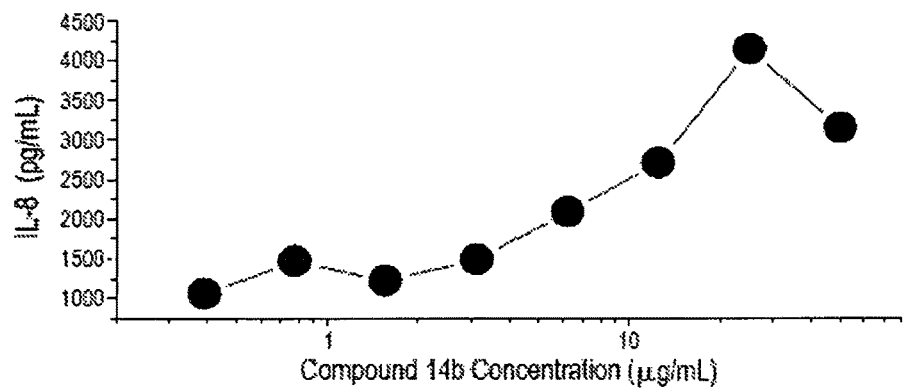
Figure 3E:
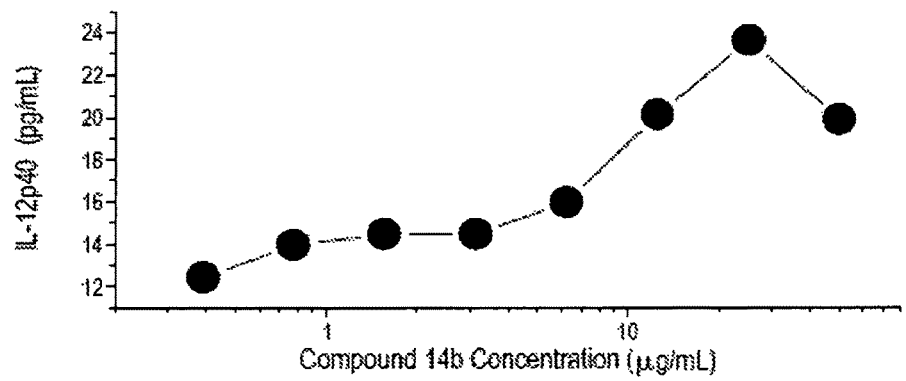
Figure 3F:
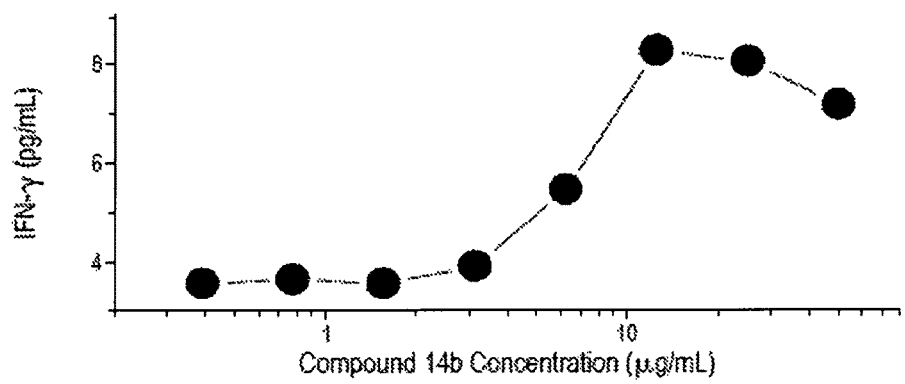
Figure 3G:
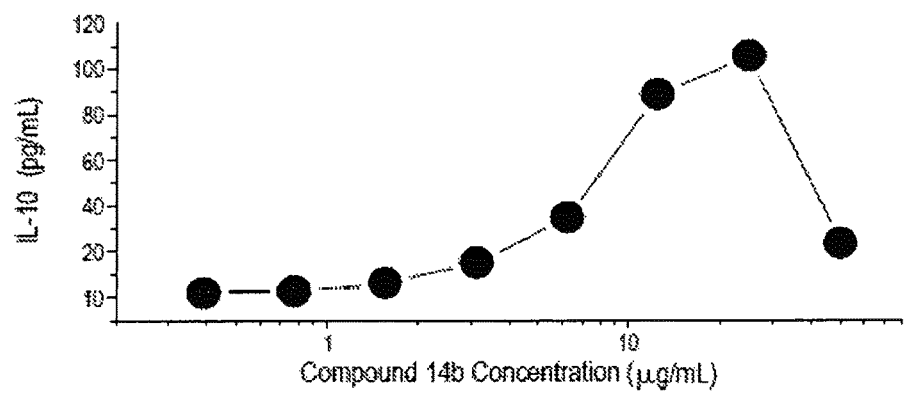
Figure 3H:
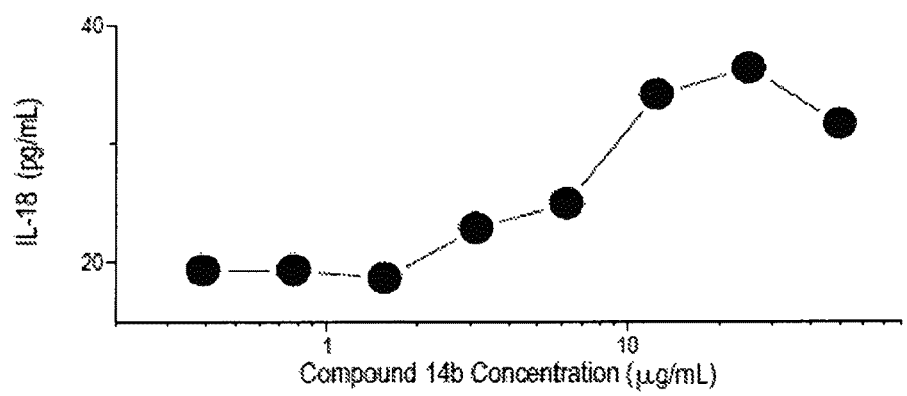
Figure 3I:
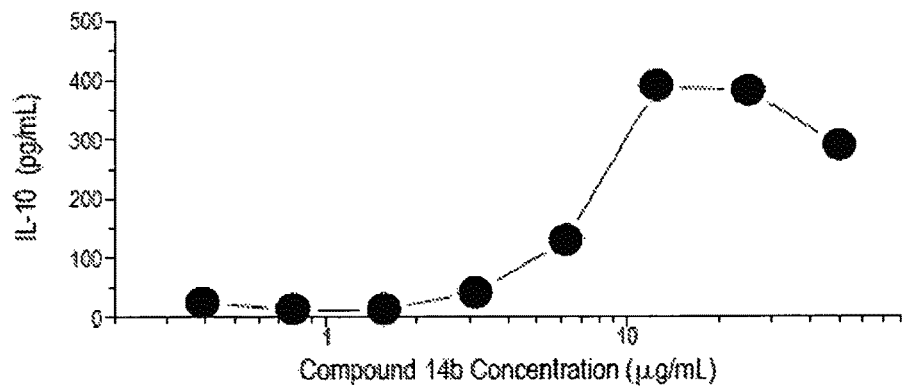
Figure 3J:
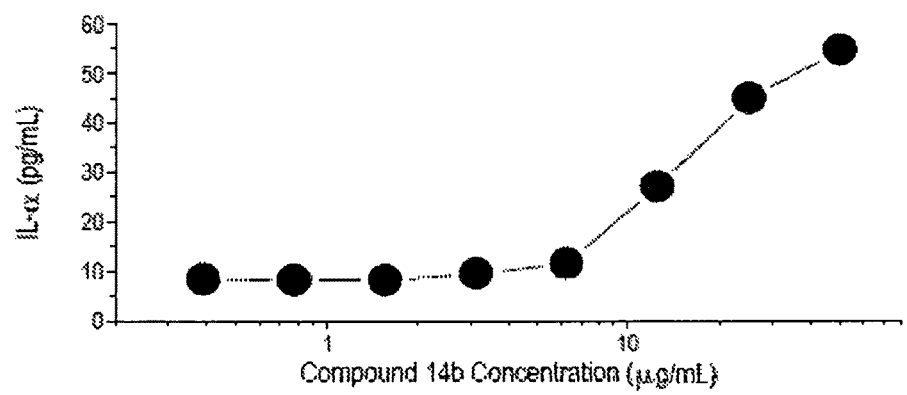
Figure 3K:
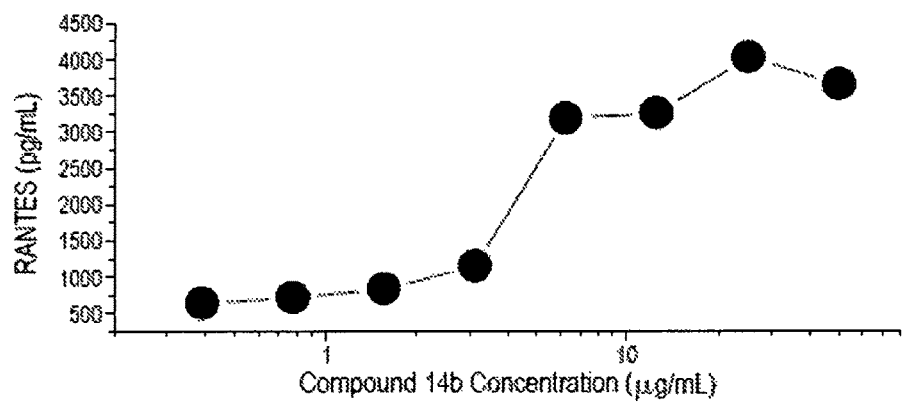
Figure 3L:
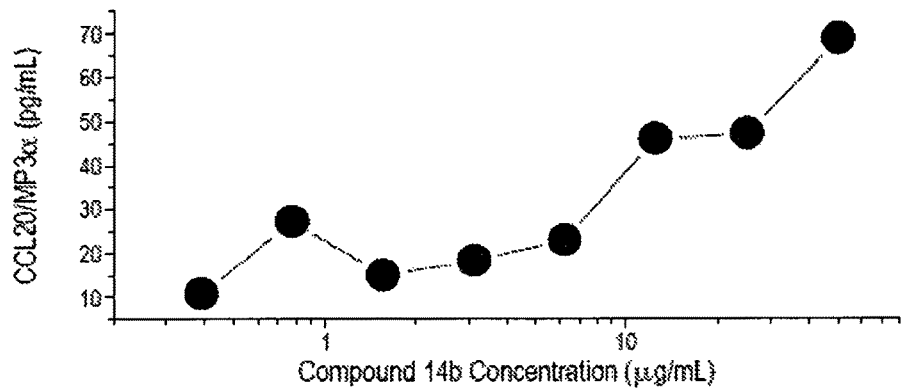
Figure 3M:
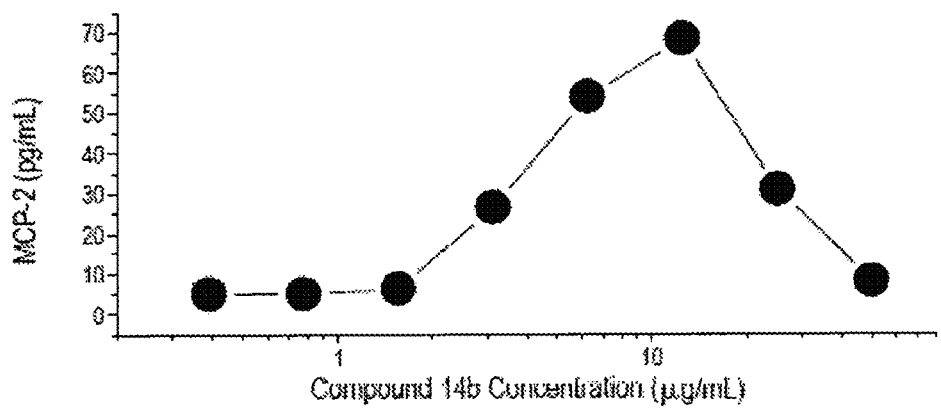
Figure 3N:
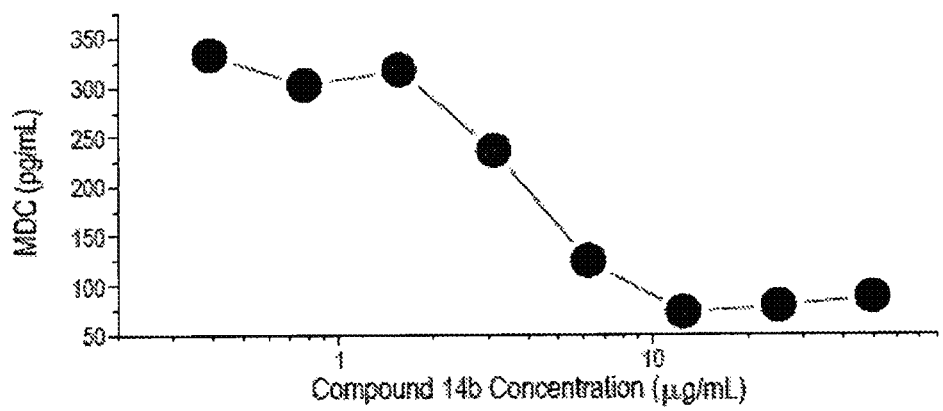
Figure 3O:
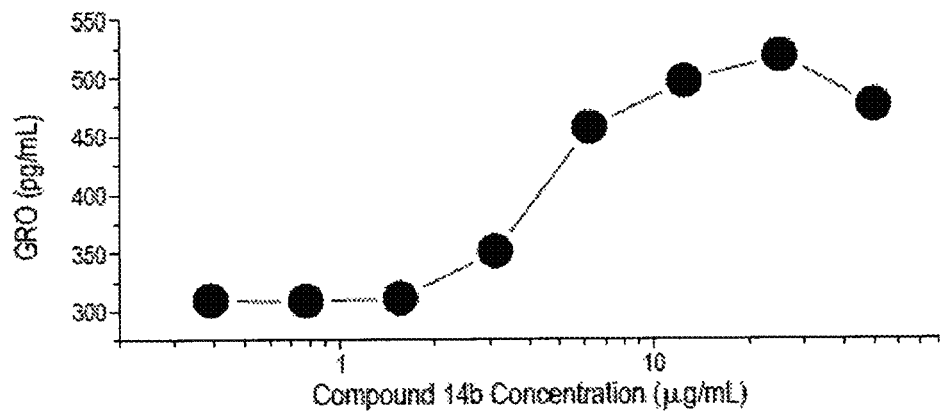
Figure 3P:
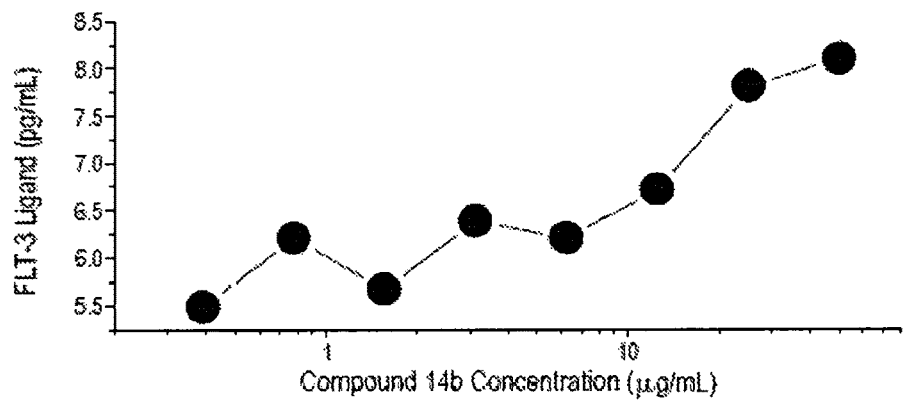
Figure 3Q:
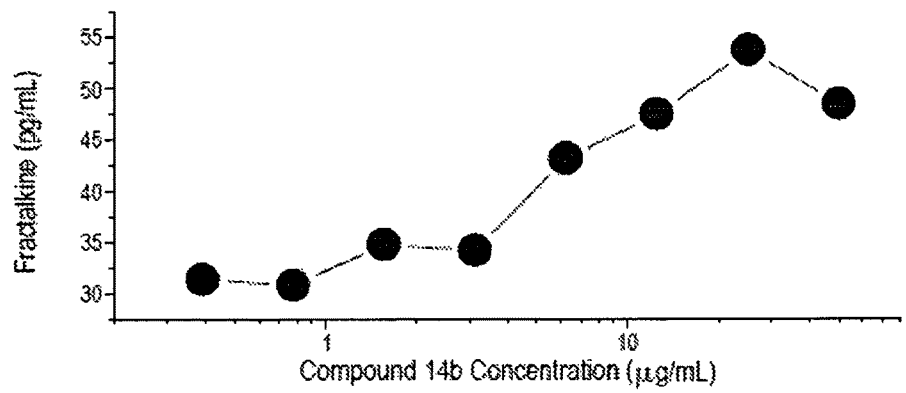
Figure 3R:
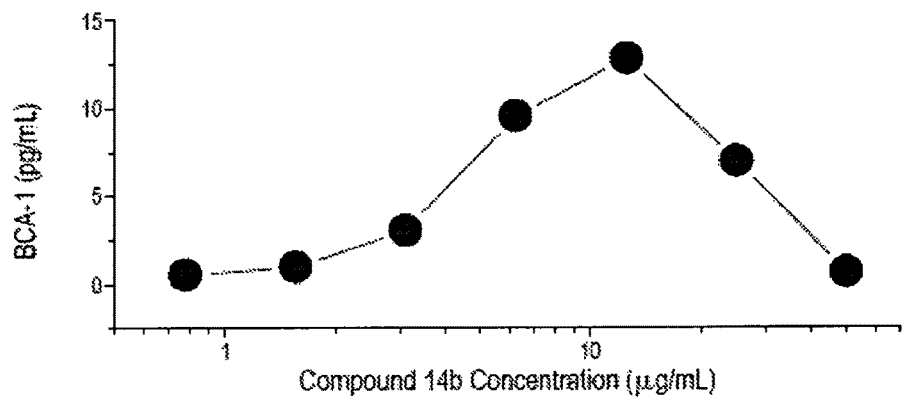
Figure 3S:
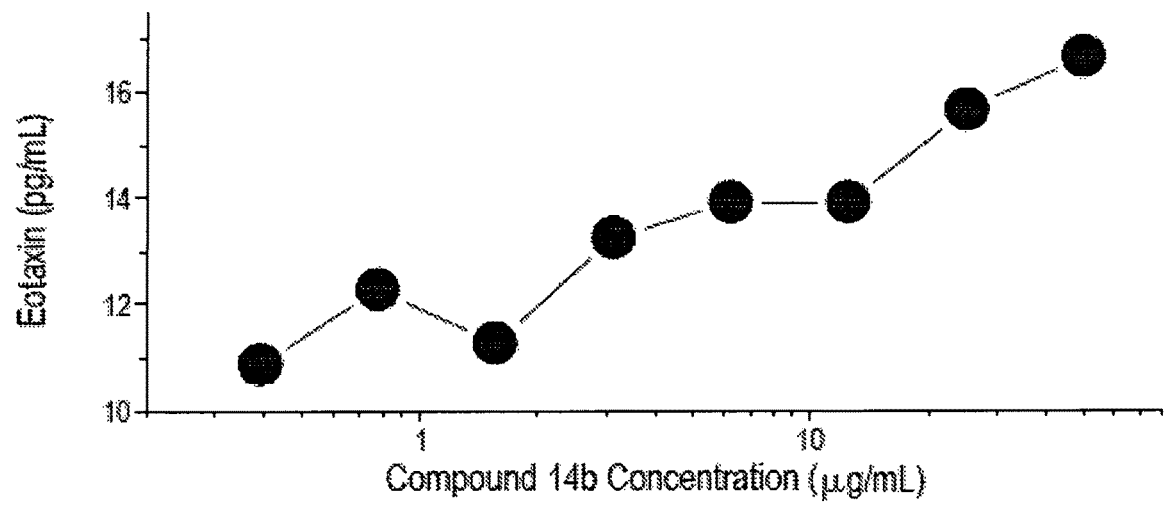
Figure 3T:
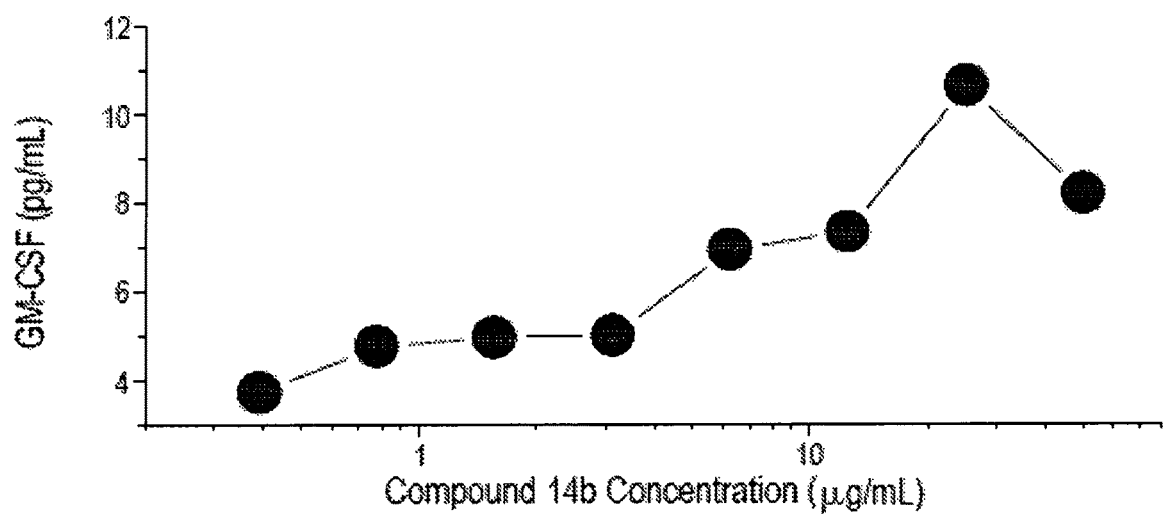

FIGS. 3A-3T show the induction of cytokines and chemokines in human PBMCs by the lead Compound 14b.

Thus, strategic compound design utilized the structure of TLR8 complexed with ligands in the rational design of a novel TLR8-specific chemotype which retains prominent cytokine-inducing activity profiles in ex vivo human blood assay systems, paving the way for evaluation of this compound as a candidate vaccine adjuvant in appropriate animal models.

Also, human T-regulatory cells (Tregs), classified immunophenotypically as naturally occurring (CD4$^+$CD25$^+$ Foxp3$^+$) or induced (CD4$^+$CD25$^{high}$), down-regulate and suppress a broad array of immune responses, including the non-specific suppression of both CD4$^+$ and CD8$^+$ T-cells via cell-cell contact and via production of immunosuppressive cytokines such as IL-10 and TGF-β. Tregs express abundant TLR8 mRNA, and TLR8 agonists have been shown to reverse Treg function via a TLR8-MyD88 (myeloid differentiation factor 88)-IRAK4 (IL-1-receptor-associated kinase 4) signaling pathway. Engagement and activation of TLR8, such as the compounds herein, strongly induces innate immunity and enhances adaptive immunity.

Driven by the need to identify pure TLR8 agonists also capable of inducing IL-12 and IL-18, and drawing from earlier work in delineating structure-activity relationships in the furo[2,3-c]pyridines, a variety of fused heterocyclic core structures were investigated. Continuing investigations have led to the discovery of pure TLR8-agonistic activity associated with strong interferon-γ (IFN-γ, IL-12 and IL-18 inducing activities in a series of furo[2,3-c]quinolones as described herein. The 4-amino-furo[2,3-c]quinoline chemotype is unprecedented in the literature, and the activity profile of this class of compounds, examined by a range of secondary screens in human ex vivo blood models, including transcriptomal profiling, confirm pure TLR8 agonism with no detectable signatures of TLR7 activity, allowing the evaluation of such compounds as potential adjuvants for vaccines.

Benzologues of the furo[2,3-c]pyridines were investigated. It was determined that the furo[2,3-c]quinoline and its regioisomeric core structures could be derived via one-pot Sonogashira coupling of alkynes to either 4-iodoquinolin-3-ol (Scheme 4) or 3-iodoquinolin-4-ol (Scheme 5), followed by a tandem, tethered nucleophile-assisted, intramolecular 5 endo-dig cyclization.

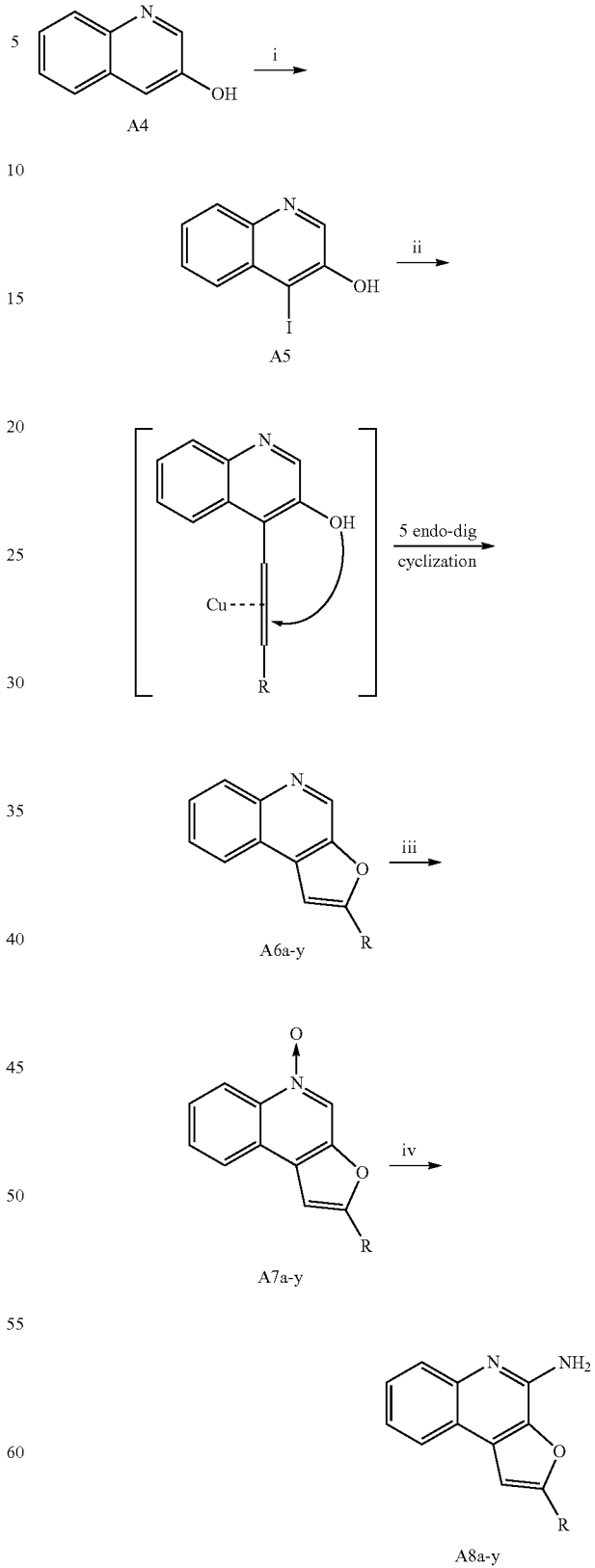

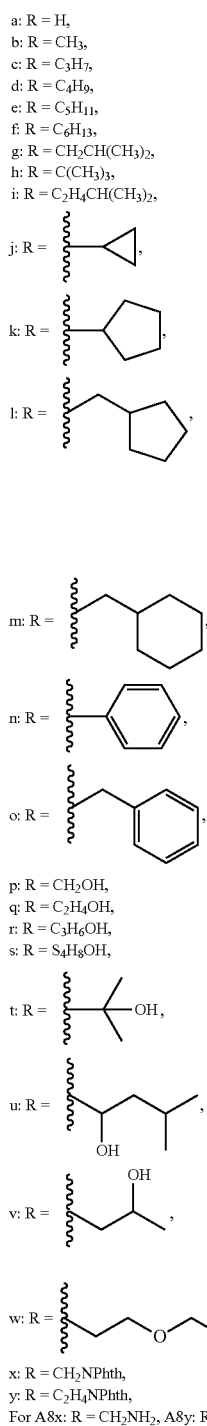

a: R = H,
b: R = CH₃,
c: R = C₃H₇,
d: R = C₄H₉,
e: R = C₅H₁₁,
f: R = C₆H₁₃,
g: R = CH₂CH(CH₃)₂,
h: R = C(CH₃)₃,
i: R = C₂H₄CH(CH₃)₂, j: R = cyclopropyl, k: R = cyclopentyl, l: R = CH₂-cyclopentyl, m: R = CH₂-cyclohexyl, n: R = phenyl, o: R = CH₂-phenyl, p: R = CH₂OH,
q: R = C₂H₄OH,
r: R = C₃H₆OH,
s: R = S₄H₈OH, t: R = C(CH₃)₂OH, u: R = CH(OH)CH(CH₃)₂, v: R = CH₂CH(OH)CH₃, w: R = CH₂CH₂OC₂H₅, x: R = CH₂NPhth,
y: R = C₂H₄NPhth,
For A8x: R = CH₂NH₂, A8y: R = C₂H₄NH₂

Scheme 4 shows the synthesis of C2-alkylfuro[2,3-c] quinoline analogues. Reagents: (i) I₂, KI, NaOH; (ii) Pd(PPh₃)₄, CuI, alkyne, Et₃N:CH₃CN (1:3); (iii) m-CPBA, CHCl₃; (iv) (a) benzoyl isocyanate, CH₂Cl₂, (b) NaOCH₃, MeOH.

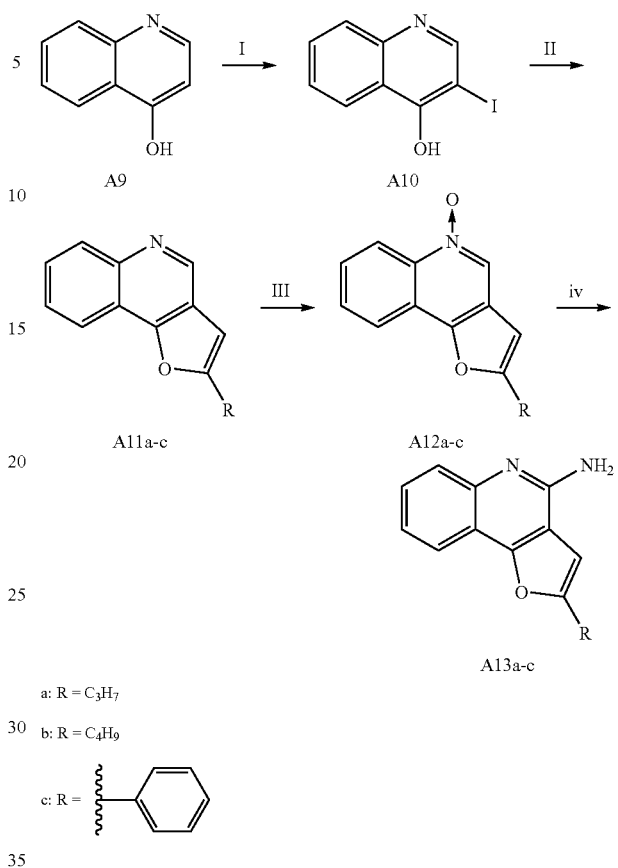

Scheme 5 a: R = C₃H₇
b: R = C₄H₉ c: R = phenyl

Scheme 5 shows the synthesis of C2-alkylfuro[3,2-c] quinoline analogues. Reagents: (i) I₂, KI, NaOH; (ii) Pd(PPh₃)₄, CuI, alkyne, Et₃N:CH₃CN (1:3); (iii) m-CPBA, CHCl₃; (iv) (a) benzoyl isocyanate, CH₂Cl₂, (b) NaOCH₃, MeOH.

Figure 5A:
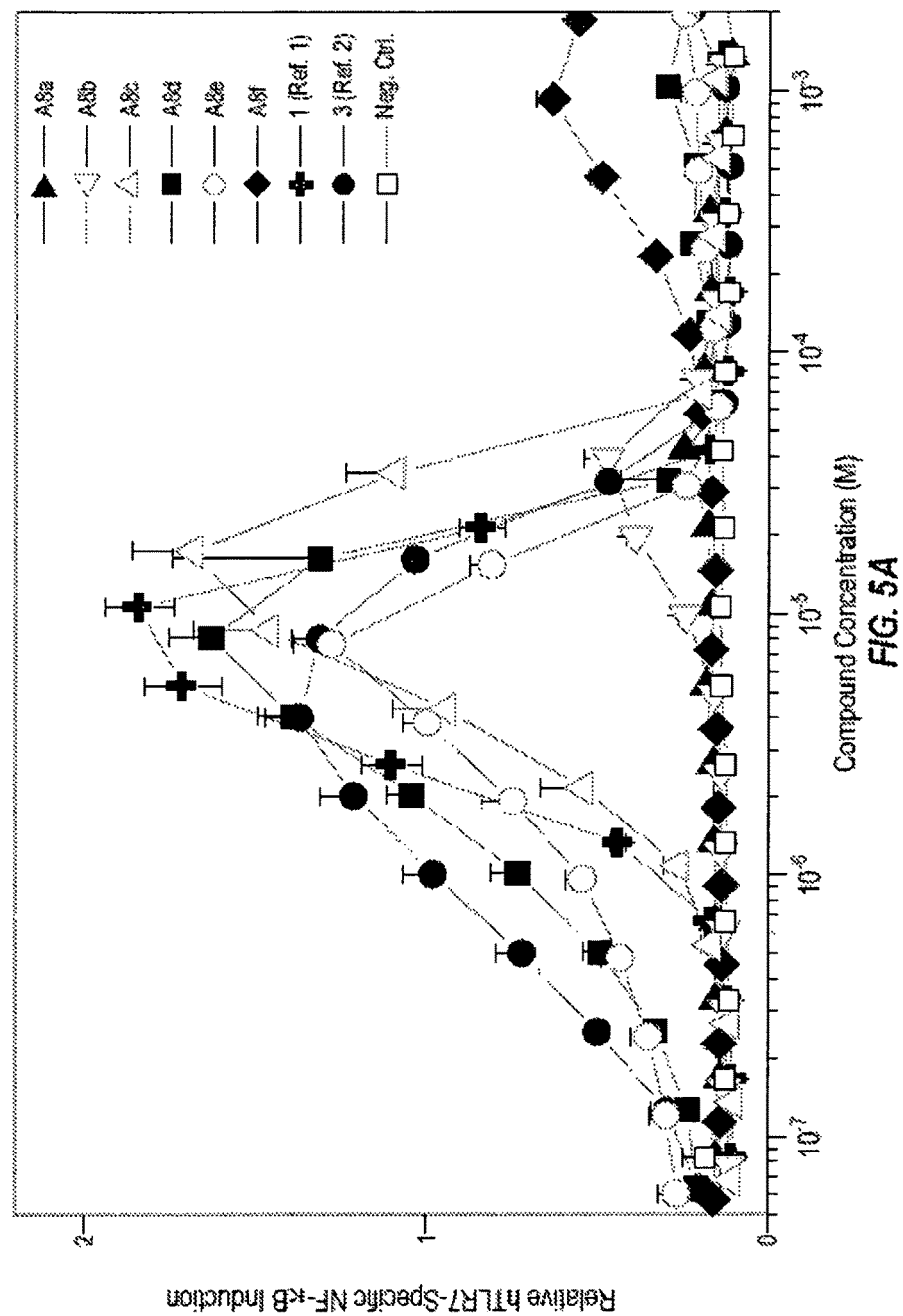
FIGS. 5A-5B include dose-response profiles of human TLR8 (FIG. 5A) and human TLR7 (FIG. 5B) agonism by select C2-alkyl furo[2,3-c]quinolones, were error bars represent standard deviations obtained on quadruplicates, and dual TLR7/8-agonistic Compounds 1 and 2 were used as comparators.
Figure 5B:
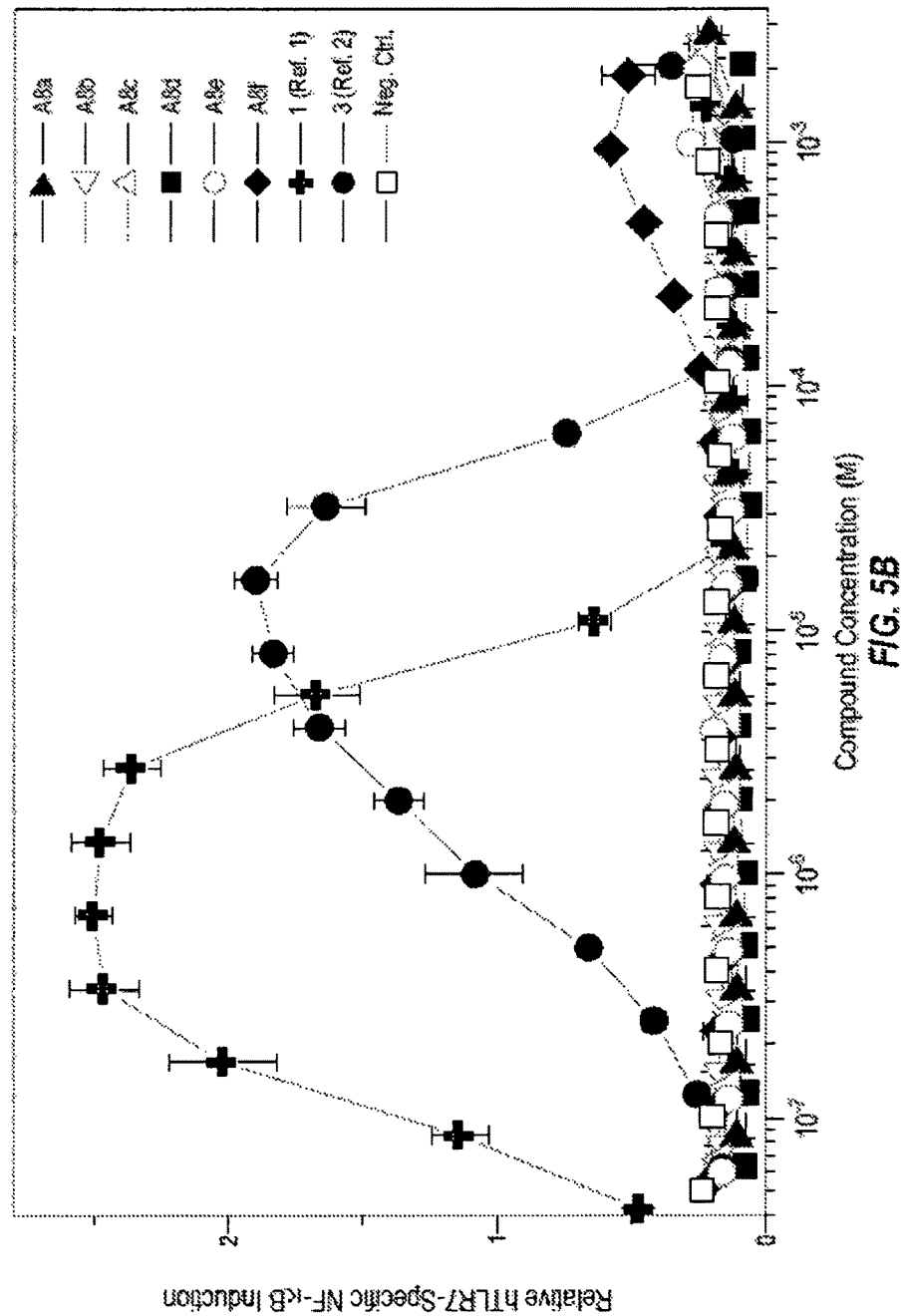
Figure 5C:
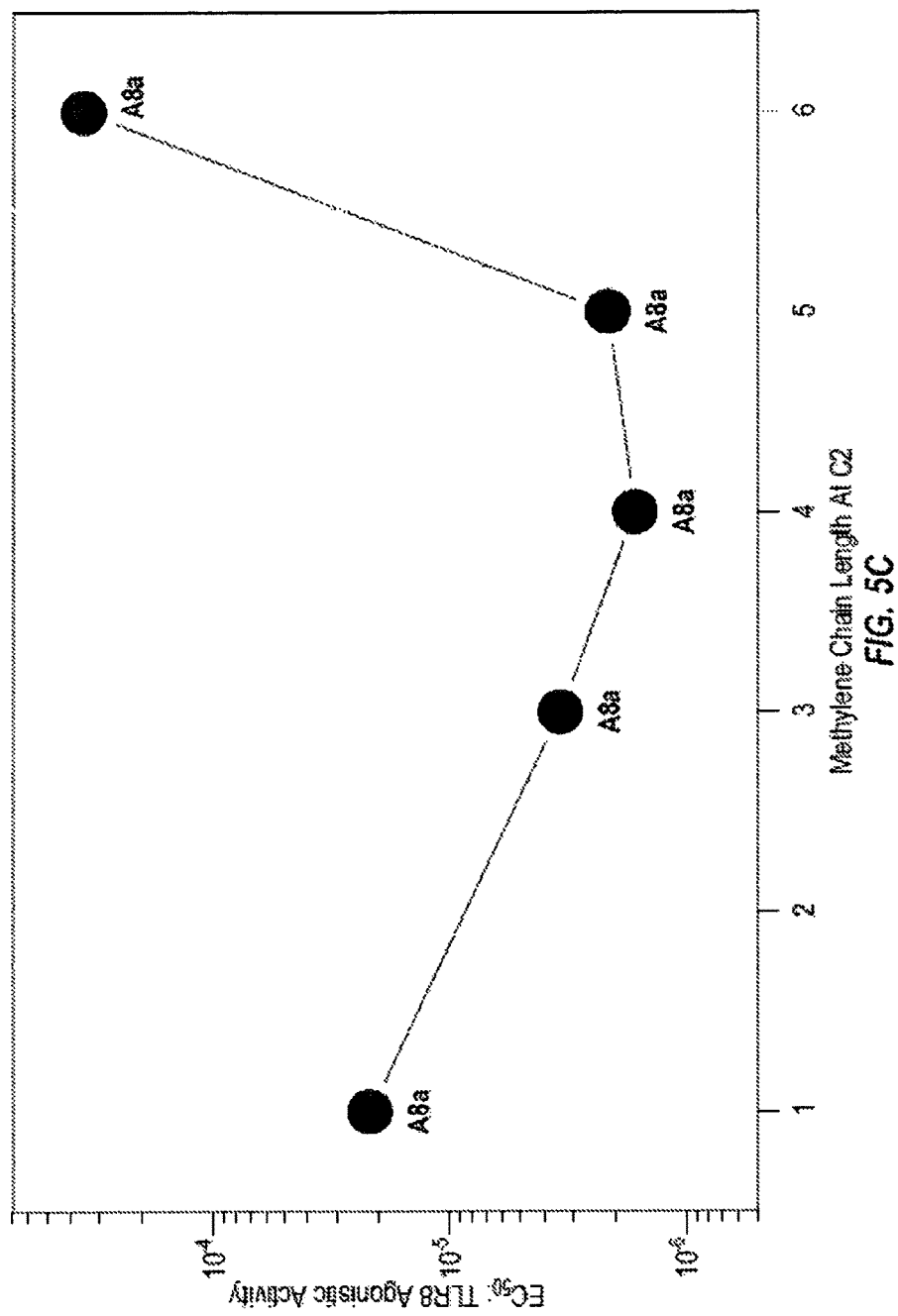
FIG. 5C shows the TLR8 agonistic activity for the compounds as a function of methylene chain length at the C2.
Figure 6A:
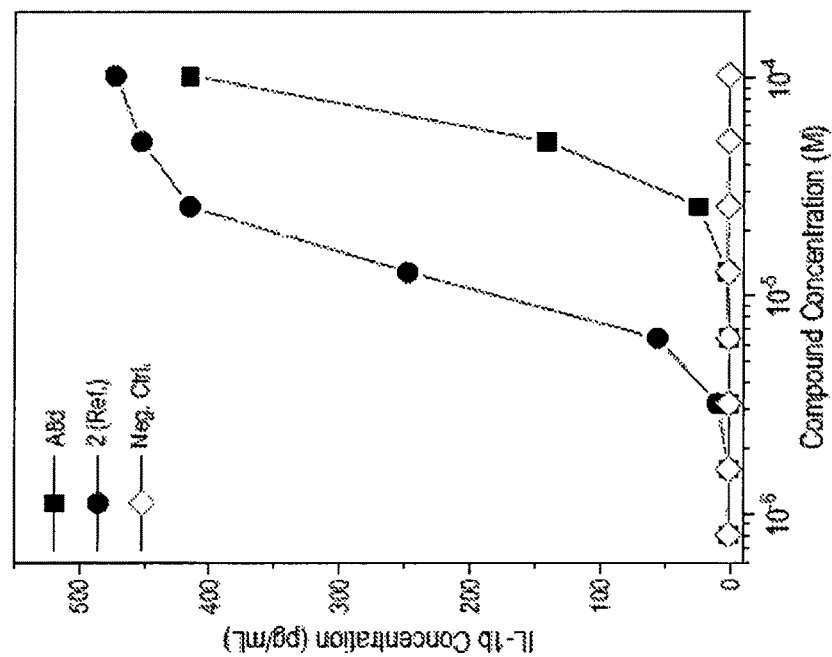
FIGS. 6A-6D include graphs that show the proinflammatory cytokine induction profiles of Compound A8d in human blood, where Compound 2 was used as reference/comparator compound.
Figure 6B:
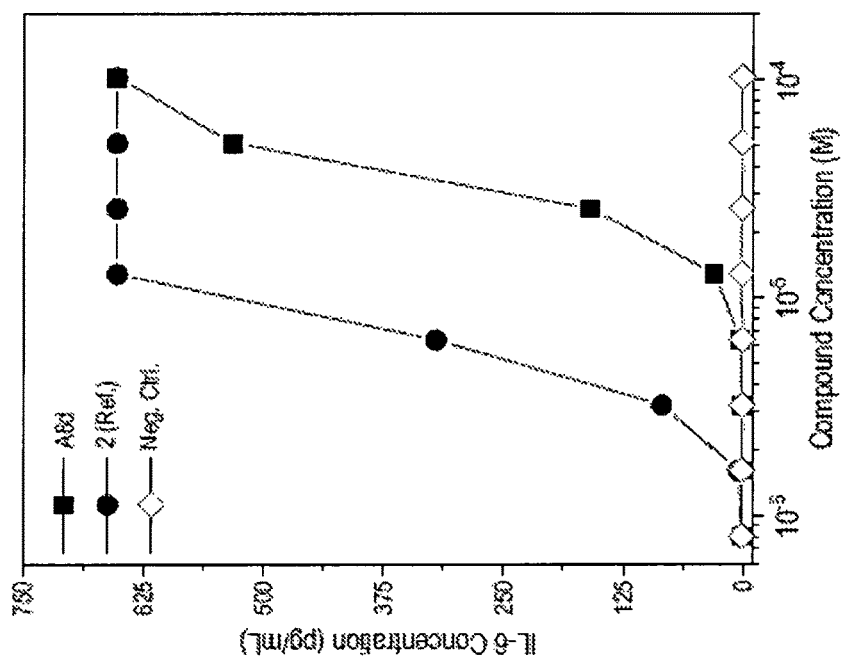
Figure 6D:
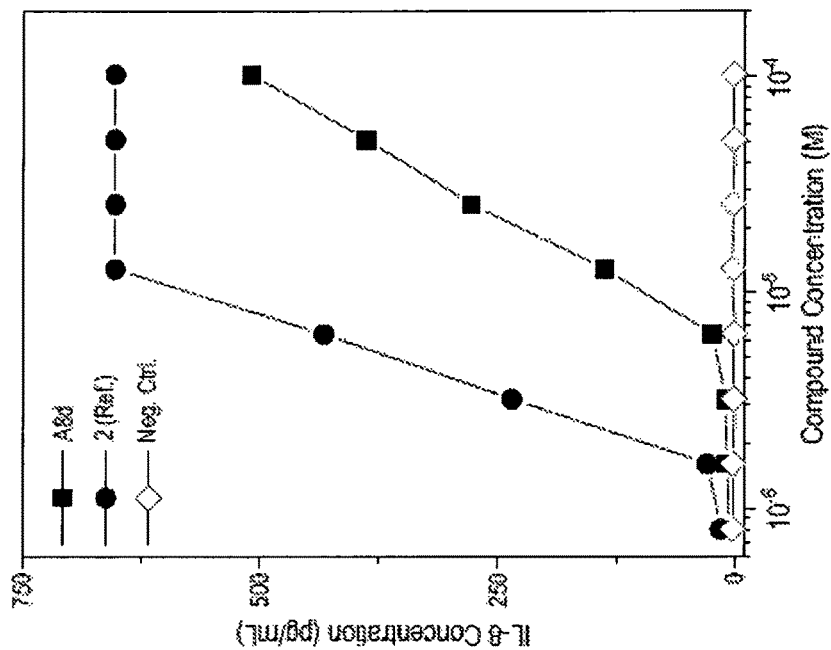
Figure 6C:
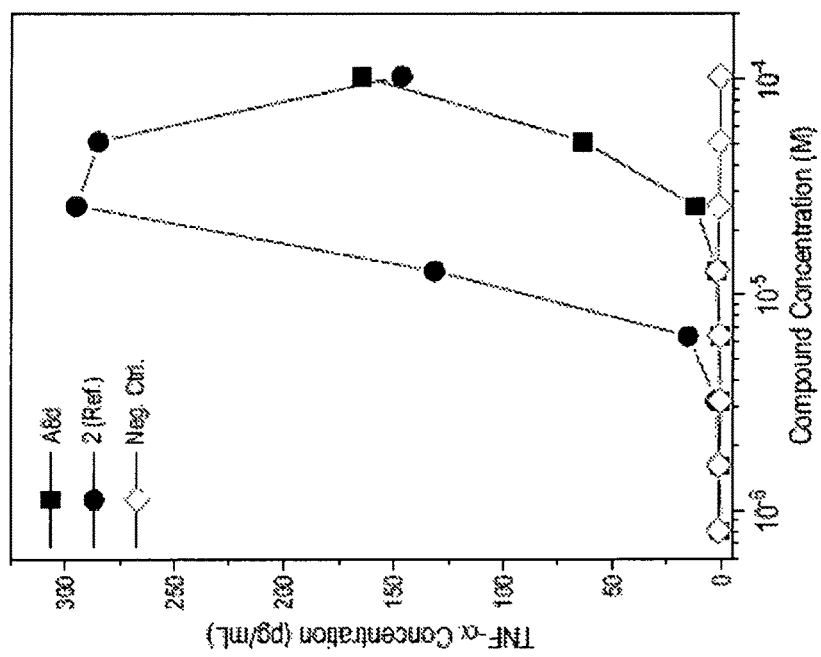

Electrophilic iodination of commercially-available 3- and 4-hydroxyquinoline proceeded using reported methods (Scheme 4 and 5). One-pot Sonogashira coupling with a variety of alkynes, followed by 5-endo-dig cyclization yielded compounds the 2-substituted furo[2,3-c]quinolines Compounds A6a-y (Scheme 4) and the regioisomeric furo[3,2-c]quinolines Compounds A11a-c (Scheme 5) in good yields. The target Compounds A8a-y and A13a-c bearing 4-amino groups were obtained using conventional procedures. Compounds A8a-y and A13a-c were screened in a panel of reporter gene assays for human TLR2/3/4/5/7/8/9 and NOD1/2 modulatory activities. A distinct activity profile was observed in the very first set of compounds that were synthesized. Compounds A8b-f showed pure TLR8 agonistic activity with maximal potency exhibited by Compound A8d with a C2-butyl group ($EC_{50}$: 1.6 μM, FIGS. 5A-5C); shorter (Compounds A8b, A8c) and longer (Compounds A8e, A8f) homologues displayed lower agonistic potencies with the shortest analogue Compound A8a being inactive (FIGS. 5A-5B). The dose-response profiles show characteristic biphasic responses (dose-dependent activation, followed by apparent suppression of NF-κB translocation, FIG. 5A-5B) as we had previously observed in several chemotypes. Accordingly, the compounds of the invention can exclude Compound A8a.

In one embodiment, the compounds of the invention exclude those compounds that are not agonists of TLR8.

Figure 7A:
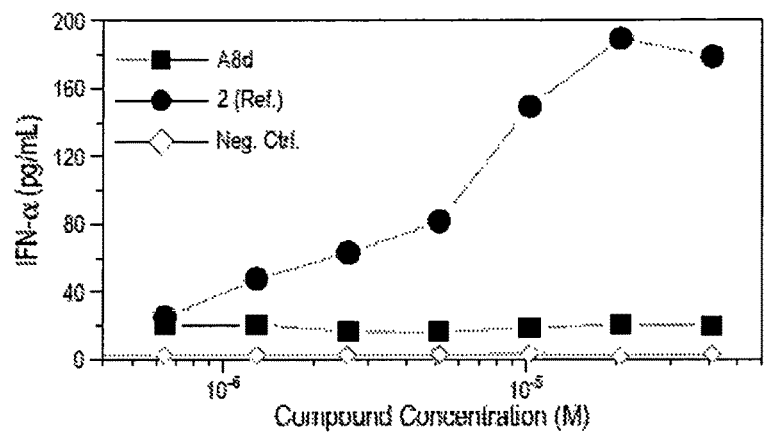
FIGS. 7A-7C include graphs that show the dose-response profiles of IL-12p40 and IL-18 induction and the absence of IFN-α by Compound A8d, where Compound 2 was used as reference/comparator compound.
Figure 7B:
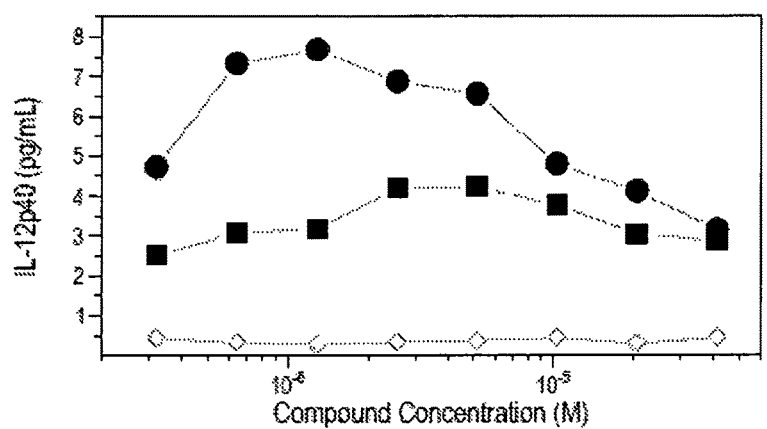
Figure 7C:
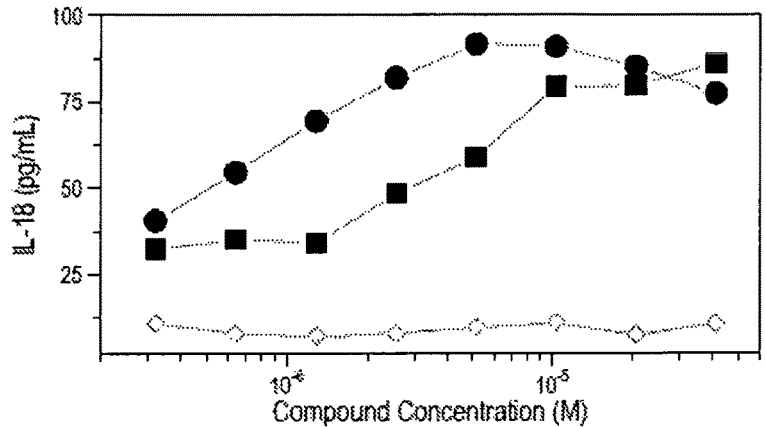
Figure 8:
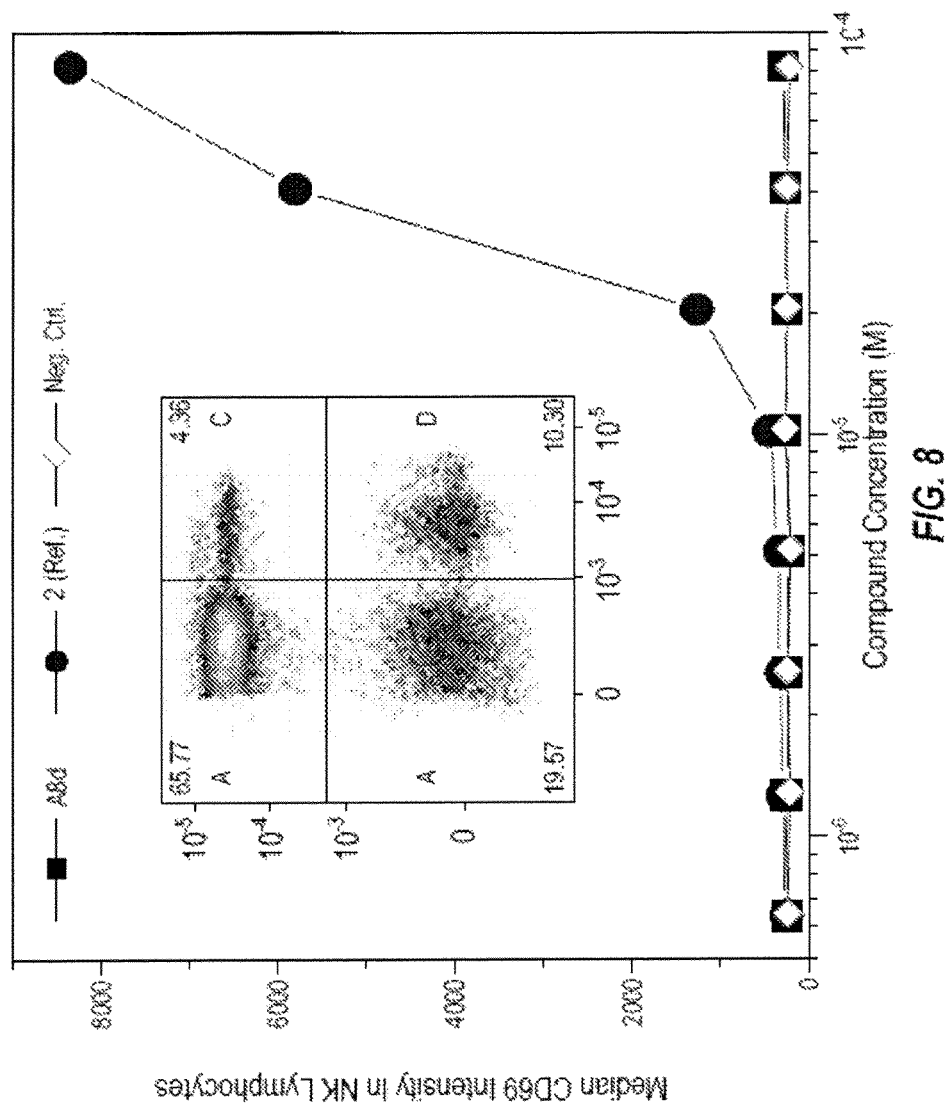
FIG. 8 includes a graph that shows the absence of CD69 upregulation in human natural killer cells by Compound A8d, and the inset shows gating on lymphocytes showing $CD3^+CD56^-$ (T cells, Quadrant A), $CD3^-CD56^-$ (nominal B cells, Quadrant B), $CD3^+CD56^+$ (cytokine-induced killer cells, Quadrant C), and $CD3^-CD56^+$ (natural killer cells, Quadrant D).

The SAR pattern with maximal activity conferred by a C2-butyl group is virtually identical to that found in TLR7-active imidazoquinolines, and the TLR8/7-agonistic thiazoloquinolines, but unlike the thiazoloquinolines, Compound A8d was devoid of TLR7-stimulatory activities in primary screens (FIG. 5B). The exquisite selectivity for TLR8 was confirmed in secondary screens using ex vivo whole human blood and PBMC models. It has been shown that proinflammatory cytokine induction (TNF-α, IL-1β, IL-6 and IL-8) is a consequence of TLR8 activation. Th1-biasing IL-12 and IL-18 induction is also TLR8-dependent, while IFN-α production is TLR7-mediated. Experiments examined cytokine and interferon induction profiles of Compound A8d, employing the thiazoloquinoline Compound 2 as a reference compound. Unlike the 2,3-diamino-furo[2,3-c]pyridines, Compound A8d was observed to induce TNF-α, IL-β, IL-6 and IL-8 in a dose-dependent manner, albeit with a lower potency than Compound 2 (FIGS. 6A-6D). Compound A8d induced IL-12 and IL-18, but was bereft of IFN-α-inducing properties (FIGS. 7A-7C). The selectivity of Compound A8d for TLR8 was also reflected in the absence of natural killer lymphocyte activation in human whole blood models as assessed by CD69 expression (FIG. 8), which had previously shown to be TLR7-dependent. Consistent with the above findings, transcriptomal profiling experiments showed strong induction of proinflammatory cytokine transcripts (including IL-12 and IL-18) by both Compound 2 and Compound A8d, but IFN-α transcription was induced only by Compound 2, owing to its dual TLR8/7 agonistic activity. These data collectively confirm the selectivity of Compound A8d for human TLR8.

Figure 9:
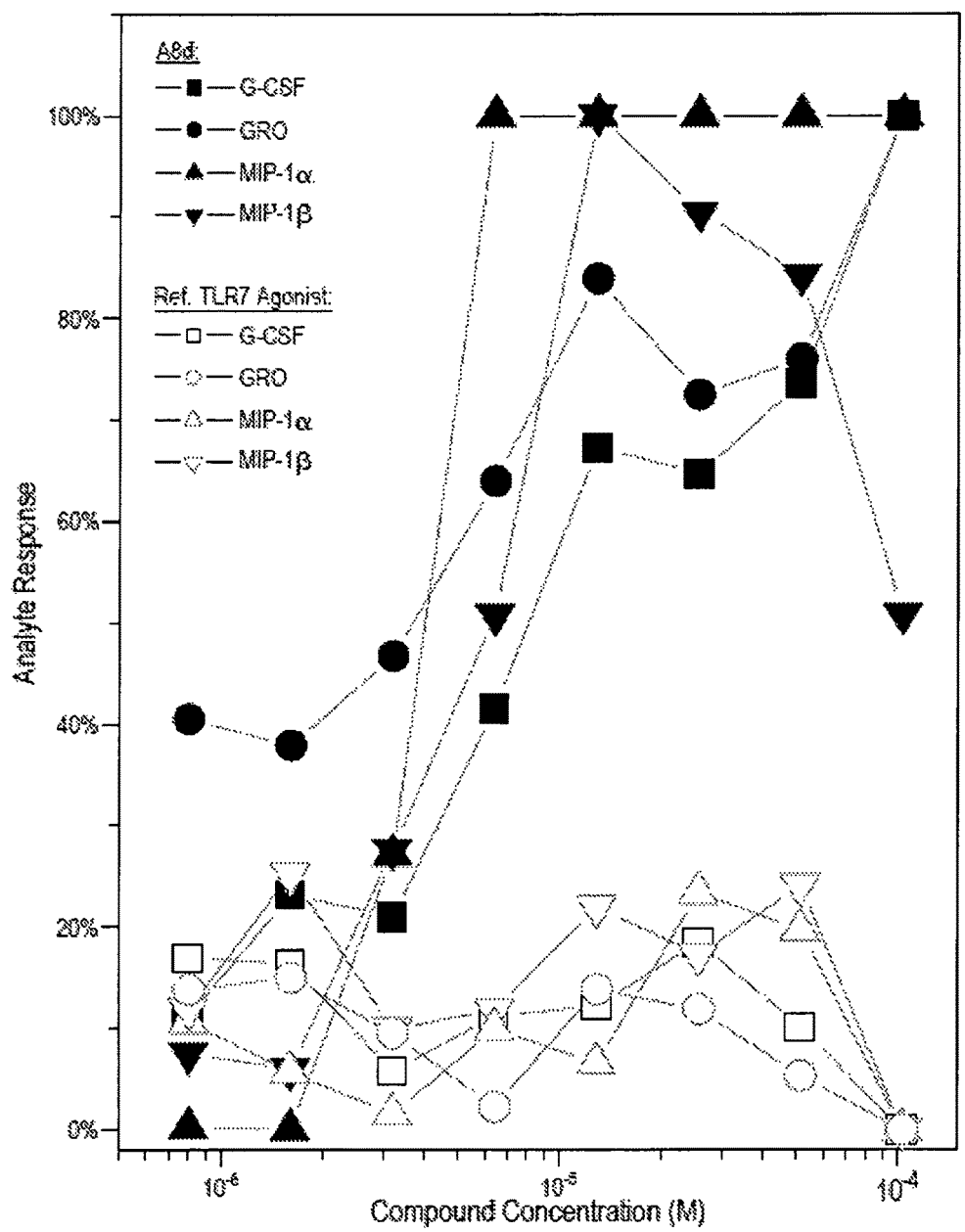
FIG. 9 includes a graph that shows the disparate responses in select analytes (out of 41 analytes) in human PBMCs. G-CSF, GRO, MIP-1α, and MIP-1β are induced by Compound A8d (and Compound 2, data not shown), but not by a pure TLR7 agonistic imidazoquinoline, where dose responses represent percent maximal response (G-CSF: 622 pg/mL, GRO: 515 pg/mL, MIP-1α: 10780 pg/mL, and MIP-1β: 10374 pg/mL).

Given that Compound A8d represents an optimized compound in a uniquely TLR8-specific chemotype, experiments profiled cytokine- and chemokine-inducing properties using a 41-analyte, multiplexed assay, comparing Compound A8d to a variety of TLR agonists. Experiments found that of the 41 analytes analyzed, whereas both Compound A8d and Compound 2 induced granulocyte colony-stimulating factor (G-CSF), growth-related oncogene (GRO), and macrophage inflammatory proteins 1-α and -β (MIP-1α, MIP-1β), a highly potent, pure TLR7-agonistic imidazoquinoline (1-benzyl-2-butyl-1H-imidazo[4,5-c]quinolin-4-amine) that we had identified in our earlier SAR studies did not, indicating that this set of analytes could be useful in distinguishing TLR8-specific responses, which is shown in FIG. 9.

C2 substituents with branched alkyl groups (Compound A8g-A8i) abrogated activity, and analogues with cycloaliphatic (Compounds A8j-A8m) or aromatic (Compounds A8n, A8o) substituents were inactive, pointing to intolerance of steric bulk at the putative binding site(s). Experiments examined a number of analogues bearing hydroxyl groups at various positions along the C2-alkyl chain (Compounds A8p-A8v), compounds with C2 substituents terminating with a primary amine (Compounds A8x, A8y), as well as an analogue with an ether (H-bond acceptor) incorporated in the alkyl group (Compound A8w), but none of these compounds were active in any primary screens. Accordingly, the compounds of the invention can exclude Compounds A8j-A8y. On the other hand, Compounds A8g-A8i can be included or omitted.

Key regioisomeric furo[3,2-c]quinolones such as Compounds A13a-c (Scheme 5) were prepared; these compounds were quiescent, displaying neither stimulatory nor inhibitory activity in primary screens. Thus, Compounds A13a-c can be omitted from the invention.

A furo[2,3-c]isoquinoline with a C2-butyl substituent (Compound A18, Scheme 6) was prepared in an order to explore chemical space beyond the fused-quinoline chemotypes, however, Compound A18 was inactive. Thus, Compound A18 can be omitted from the invention.

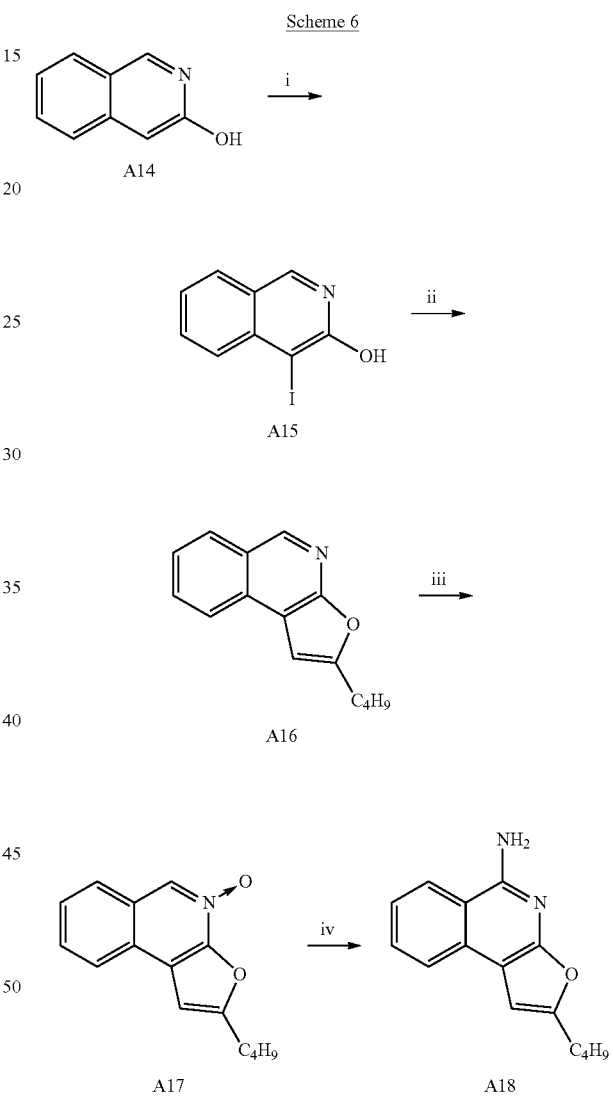

Scheme 6 shows the syntheses of C2-alkylfuro[2,3-c]isoquinoline analogues. Reagents: (i) I$_2$, KI, NaOH; (ii) Pd(PPh$_3$)$_4$, CuI, alkyne, Et$_3$N:CH$_3$CN (1:3); (iii) m-CPBA, CHCl$_3$; (iv) (a) benzoyl isocyanate, CH$_2$Cl$_2$, (b) NaOCH$_3$, MeOH.

The effect of introducing substituents at the C1 position was studied. Electrophilic bromination of Compound A7d furnished precursor Compound A19 in good yield (Scheme 7) which was carried forward to obtain both the 1-bromo- and 1-benzyl-substituted analogues Compounds A21 and A24, respectively (Scheme 7).

Scheme 7

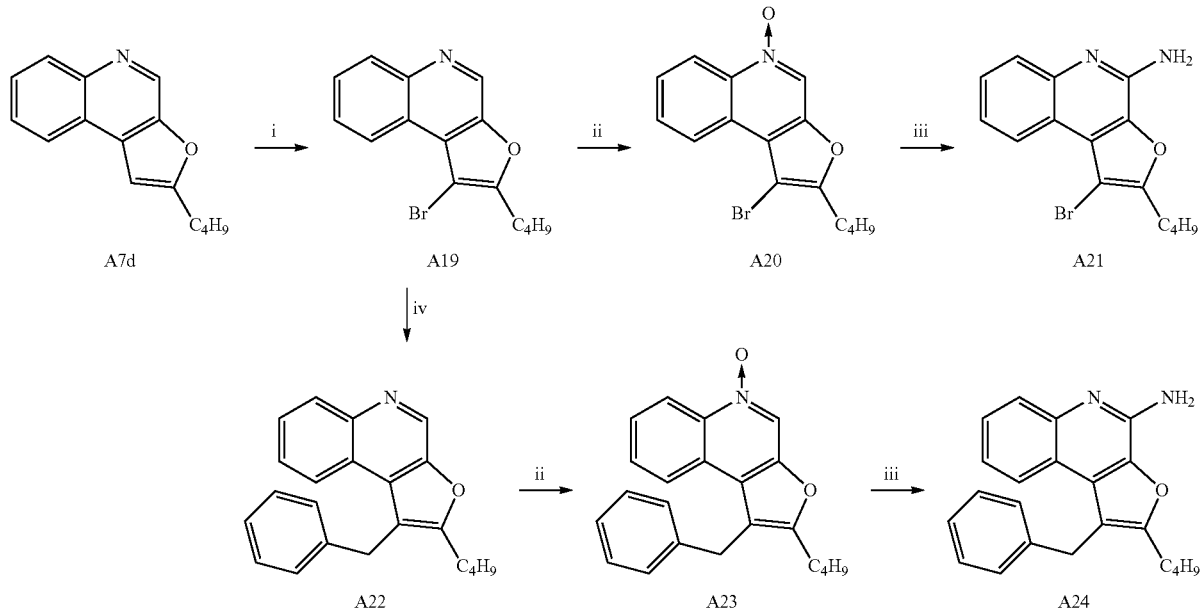

Scheme 7 shows the syntheses of C1-substituted furo[2,3-c]quinoline analogues. Reagents: (i) Br$_2$, CH$_2$Cl$_2$; (ii) m-CPBA CHCl$_3$; (iii) (a) benzoyl isocyanate, CH$_2$Cl$_2$, (b) NaOCH$_3$, MeOH; (iv) Pd(dppf)Cl$_2$, 2-benzyl-4,4,5,5-tetramethyl-1,3,2-dioxaborolane, Cs$_2$CO$_3$, 1,4-Dioxane Two compounds (Compound A28a, A28b) were therefore synthesized (Scheme 8). Both these analogues retained TLR8-selective agonistic activities, but were substantially weaker (EC$_{50}$: 24.4 μM and 46.2 μM, respectively) than Compound A8d (EC$_{50}$: 1.6 μM).

Scheme 8

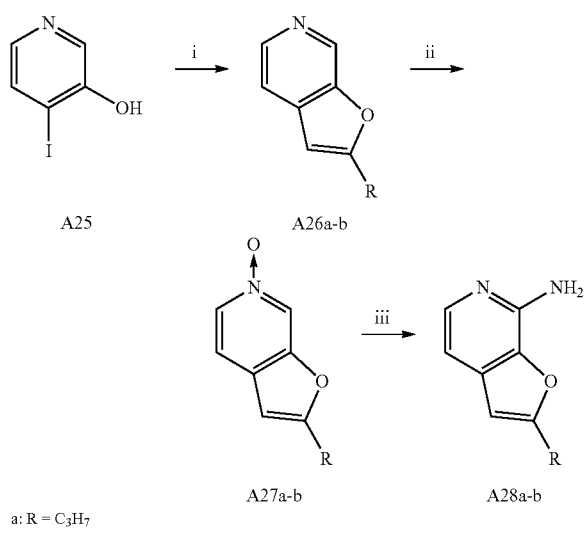

a: R = C$_3$H$_7$
b: R = C$_4$H$_9$

Scheme 8 shows syntheses of C2-alkylfuro[2,3-c]pyridine analogues. Reagents: (i) Pd(PPh$_3$)$_4$, CuI, alkyne, Et$_3$N: CH$_3$CN (1:3); (ii) m-CPBA, CHCl$_3$; (iii) (a) benzoyl isocyanate, CH$_2$Cl$_2$, (b) NaOCH$_3$, MeOH.

Strong ionic H-bonds (salt bridges) are observed between the C4-amine of both Compound 2 and Compound A8d with Asp543 of protomer B, with additional stabilization derived from a H-bond between Thr574 (protomer B) and either the N$^2$ atom of the thiazole ring of Compound 2 or the oxygen atom of the furanyl ring of Compound A8d. π-π interactions of the quinoline moiety of Compound 2 and Compound A8d (Phe405/Tyr353), as well as hydrophobic interactions of the C2-alkyl group (Phe346/Ile403/Gly376) occur exclusively with residues in protomer A. The butyl group of Compound A8d allows for excellent nonpolar and van der Waals contacts in the rather shallow hydrophobic cavity, and homologues with increasing C2-chain length (Compounds A8e-A8f) dock poorly with kinked and sterically unfavorable conformations of the alkyl group. Analogues with cycloaliphatic (Compounds A8j-A8m) and aromatic substituents (Compounds A8n, A8o) do not fit well in the hydrophobic pocket. The cavity is lined entirely with sidechains of hydrophobic residues, explaining why even length-optimized analogues bearing polar groups at the C2 position such as Compounds A8r, A8u and A8v do not display TLR8 agonism. The feeble activity of the furopyridine Compounds A28a and A28b imply significant contributions in binding free energies by t-n interactions of the quinoline moiety with Tyr353 and Phe405. The imposition of additional steric bulk at C1 (Compound A24) is not tolerated in the cleft bounded by Phe261 and Ser352. Not only is pivotal ionic H-bond between the C4-amine of regioisomeric furo[3,2-c]quinoline Compound A13b and Asp543 weakened (3.8 Å), the additional H-bond between the oxygen atom of the furan ring and Thr574 is lost entirely, forcing Compound A24 to bind to TLR8 in an inverted fashion, with the C2-alkyl group facing the entrance to the binding site. Highly unfavorable H-bonds are also seen in the isoquinolines analogue Compound A18, especially with the loss of H-bonding of the furanyl oxygen.

Accordingly, furo[2,3-c]quinolines have yielded pure TLR8 agonists, which are expected to possess strong Th1-biasing adjuvantic properties as evidenced by prominent IL-12 and IL-18 induction profiles, and are entirely without IFN-α inducing properties, confirming its exquisite selectivity for human TLR8.

In one embodiment, a compound can include a structure of Formula 7 or 7A or prodrug, salt, stereoisomer, tautomer, polymorph, solvate, or combination thereof.

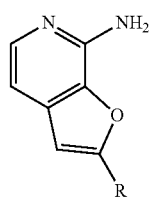

Formula 7

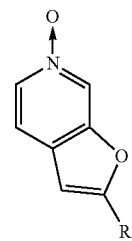

Formula 7A

In Formulae 7 or 7A, R is $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphine. In one aspect, R is $CH_3$, $C_2H_5$, $C_3H_7$ or $C_4H_9$.

In one embodiment, a pharmaceutical composition can include a compound from one of the embodiments and a pharmaceutically acceptable carrier. In one aspect, the composition is configured for oral administration, parenteral administration, intravenous administration, topical administration, or subcutaneous administration. In one aspect, the compound is present in an amount sufficient for agonizing a Toll-Like Receptor 8 (TLR8). In one aspect, the composition also includes a vaccine agent.

In one embodiment, a method of agonizing a Toll-Like Receptor 8 (TLR8) can include providing a compound of one of the embodiments to a TLR8 in an amount sufficient to agonize the TLR8.

In one embodiment, a method of improving vaccination can include administering a vaccine agent to a subject along with a compound of one of the embodiments in an amount sufficient to function as an adjuvant with regard to the vaccine agent. In one aspect, the method can include agonizing a Toll-Like Receptor 8 (TLR8) in the subject. In one aspect, the method includes agonizing the TLR8 so as to increase production of inflammatory cytokines. In one aspect, the method includes agonizing the TLR8 so as to up-regulate major histocompatibility complex (MHC) molecules and co-stimulatory signals in antigen-presenting cells. In one aspect, the method includes agonizing the TLR8 so as to activate natural killer (NK) cells. In one aspect, the method includes agonizing the TLR8 so as to cause an adaptive immune response to the vaccine agent. In one aspect, the method includes agonizing the TLR8 so as to induce production of T helper 1-polarizing cytokines. In one aspect, the subject is a youth under 5 years of age. In one aspect, the subject is elderly above 60 years of age. In one aspect, the compound is inactive to TLR7.

In one embodiment, a method of activating an immune system can include administering an immunological agent to a subject along with a compound of one of the embodiments in an amount sufficient to function as an adjuvant with regard to the immunological agent.

EXPERIMENTAL

Protein Expression, Purification and Crystallization:

The extracellular domain of human Toll-like receptor 8 (hTLR8, residues 27-827) was prepared as described previously,[1] and was concentrated to 16 mg/mL in 10 mM MES (pH 5.5), 50 mM NaCl. The protein solutions for the crystallization of hTLR8/Compound 3 complex contained hTLR8 (8.5 mg/mL) and Compound 3 (protein: chemical ligand molar ratio of 1:10) in a crystallization buffer containing 7 mM MES (pH 5.5), 35 mM NaCl. Crystallization experiments were performed with sitting-drop vapor-diffusion methods at 293 K. Crystals of hTLR8/3 complex were obtained with reservoir solutions containing 9-12% (w/v) PEG3350, 0.3 M potassium formate, and 0.1 M sodium citrate (pH 4.4).

Human TLR2/-3/-4/-5/-7/-8/-9 Reporter Gene Assays (NF-κB Induction):

The induction of NF-κB was quantified using human TLR2/-3/-4/-5/-7/-8/-9-specific HEK-Blue™ reporter gene assays as previously described. HEK293 cells stably co-transfected with the appropriate hTLR, MD2, and secreted alkaline phosphatase (sAP), were maintained in HEK-Blue™ Selection medium containing zeocin and normocin. Stable expression of secreted alkaline phosphatase (sAP) under control of NF-κB/AP-1 promoters is inducible by appropriate TLR agonists, and extracellular sAP in the supernatant is proportional to NF-κB induction. HEK-Blue™ cells were incubated at a density of ~$10^5$ cells/ml in a volume of 80 μl/well, in 384-well, flat-bottomed, cell culture-treated microtiter plates until confluency was achieved, and subsequently stimulated with graded concentrations of stimuli, sAP was assayed spectrophotometrically using an alkaline phosphatase-specific chromogen (present in HEK-detection medium as supplied by the vendor) at 620 nm.

Figure 4:
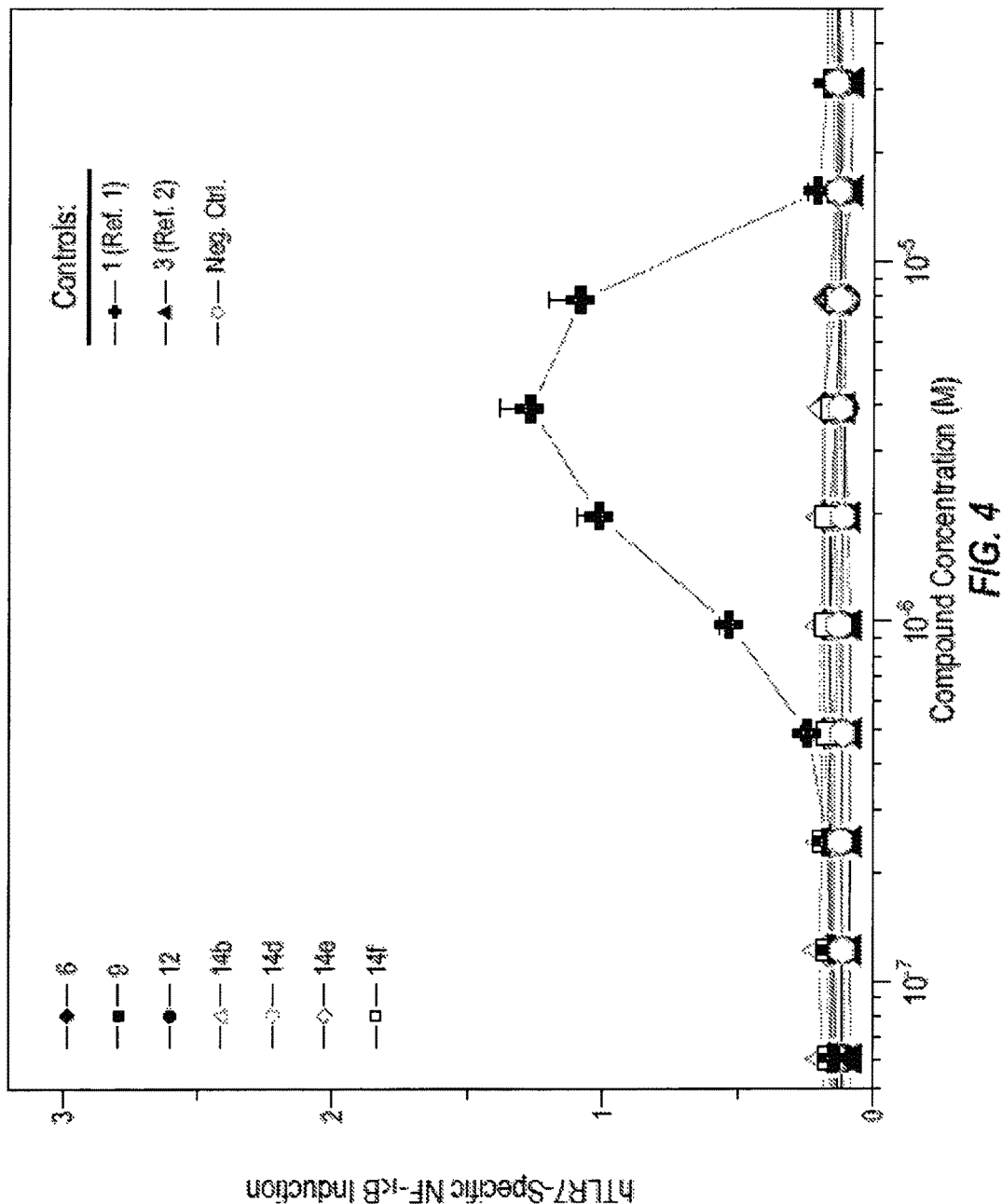
FIG. 4 includes a graph that shows data for counter-screens in human TLR7 reporter cell line of the 3-substituted 2-aminoquinolines confirm pure TLR8-agonistic activity.

FIG. 4 shows counter-screens in human TLR7 reporter cell line of the 3-substituted 2-aminoquinolines confirm pure TLR8-agonistic activity. No activity was observed in TLR2, TLR3, TLR4, TLR5, TLR7, TLR9, TLR10, Nod1 and Nod2 reporter cells (data not shown).

Immunoassays for Cytokines:

Fresh human peripheral blood mononuclear cells (hPBMC) were isolated from human blood obtained by venipuncture with informed consent and as per institutional guidelines on Ficoll-Hypaque gradients. Aliquots of PBMCs ($10^5$ cells in 100 µL/well) were stimulated for 12 h with graded concentrations of test compounds. Supernatants were isolated by centrifugation, and were assayed in triplicates using analyte-specific multiplexed cytokine/chemokine bead array assays. PBMC supernatants were also analyzed for 41 chemokines and cytokines (EGF, Eotaxin, FGF-2, Fit-3 ligand, Fractalkine, G-CSF, GM-CSF, GRO, IFN-α2, IFN-γ, IL-10, IL-12 (p40), IL-12 (p70), IL-13, IL-15, IL-17, IL-1ra, IL-1α, IL-1β, IL-2, IL-3, IL-4, IL-5, IL-6, IL-7, IL-8, IL-9, IP-10, MCP-1, MCP-3, MDC (CCL22), MIP-1α, MIP-1β, PDGF-AA, PDGF-AB/BB, RANTES, TGFα, TNF-α, TNF-β, VEGF, sCD40L) using a magnetic bead-based multiplexed assay kit (Milliplex MAP Human Cytokine/Chemokine kit). Data were acquired and processed on a MAGPIX instrument (EMD Millipore, Billerica, Mass.) with an intra-assay coefficients of variation ranging from 4-8% for the 41 analytes.

Flow-Cytometric Immunostimulation Experiments:

CD69 upregulation was determined by flow cytometry. Briefly, heparin-anticoagulated whole blood samples were obtained by venipuncture from healthy human volunteers with informed consent and as per guidelines approved by the University of Kansas Human Subjects Experimentation Committee. Aliquots of whole human blood samples were stimulated with graded concentrations of either Compound A8d or Compound 2 (used as a reference compound) in a 6-well polystyrene plate and incubated at 37° C. in a rotary (100 rpm) incubator for 16.5 h. Negative (endotoxin free water) controls were included in each experiment. Following incubation, 200 µL aliquots of anticoagulated whole blood were stained with 20 L of fluorochrome-conjugated antibodies at 37° C. in the dark for 30 min. For triple color flow cytometry experiments, CD3-PE, CD56-APC, CD69-PE-Cy7 were used to analyze CD69 activation of each of the main peripheral blood lymphocyte populations: natural killer lymphocytes (NK cells: $CD3^-CD56^+$), cytokine-induced killer phenotype (CIK cells: $CD3^+CD56^+$), nominal B lymphocytes ($CD3^-CD56^-$), and nominal T lymphocytes ($CD3^+CD56^-$). Following staining, erythrocytes were lysed and leukocytes fixed in one step by mixing 200 µL of the samples in 4 mL pre-warmed Whole Blood Lyse/Fix Buffer (Becton-Dickinson Biosciences, San Jose, Calif.). After washing the cells twice at 200 g for 8 minutes in saline, the cells were transferred to a 96-well plate. Flow cytometry was performed using a BD FACSArray instrument in the tri-color mode (tri-color flow experiment) and two-color mode (two-color flow experiment) for acquisition on 100,000 gated events. Post-acquisition analyses were performed using FlowJo v 7.0 software (Treestar, Ashland, Oreg.). Compensation for spillover was computed for each experiment on singly-stained samples.

General.

All of the solvents and reagents used were obtained commercially and used as such unless noted otherwise. Moisture- or air-sensitive reactions were conducted under nitrogen atmosphere in oven-dried (120° C.) glass apparatus. The solvents were removed under reduced pressure using standard rotary evaporators. Flash column chromatography was carried out using RediSep Rf 'Gold' high performance silica columns on CombiFlash Rf instrument unless otherwise mentioned, while thin-layer chromatography was carried out on silica gel (200 µm) CCM pre-coated aluminum sheets. Purity for all final compounds was confirmed to be greater than 97% by LC-MS using a Zorbax Eclipse Plus 4.6 mm×150 mm, 5 µm analytical reverse phase C18 column with $H_2O$-isopropanol or $H_2O$—$CH_3CN$ gradients (10-90% nonpolar phase, over 15 min) and an Agilent ESI-QTOF mass spectrometer (mass accuracy of 3 ppm) operating in the positive ion (or negative ion, as appropriate) acquisition mode. Chemical shifts are expressed in ppm (δ) and TMS was used as reference (δ=0 ppm).

General Procedure for the Synthesis of 3-(Butyloxy)quinoline (Compound 5):

To a stirred solution of quinolin-3-ol Compound 4 (299 mg, 2.06 mmol) in DMSO were added $K_2CO_3$ (569 mg, 4.12 mmol) and butyl iodide (352 µL, 3.10 mmol). The resulting reaction mixture was stirred at 80° C. for 4 h. After completion of reaction (monitored by TLC), the reaction mixture was diluted with water and extracted with diethyl ether (3×15 mL). The combined organic layer was dried over $Na_2SO_4$, concentrated under reduced pressure, and the crude material was purified by flash chromatography to obtain 5 as colorless liquid (250 mg, 60%). Compounds 5a-5i were synthesized according to the general procedure for the synthesis of Compound 5: 3-(Ethyloxy)quinoline (Compound 5b); 3-(Propyloxy)quinoline (Compound 5c); 3-(Pentyloxy)quinoline (Compound 5d); 3-(Hexyloxy)quinoline (Compound 5e); 3-(Isopropyloxy)quinoline (Compound 5f); 3-(Isobutyloxy)quinoline (Compound 5g); 3-(Isopentyloxy) quinoline (Compound 5h); and (S)-3-(2-Methylbutyloxy) quinoline (Compound 5i).

General Procedure for the Synthesis of 3-(Butyloxy)quinolin-2-amine (Compound 6):

To a stirred solution of substrate Compound 5 (200 mg, 0.1 mmol) in $CHCl_3$ was added m-CPBA (667 mg, 3.86 mmol), the resulting reaction mixture was stirred at r.t. for 4 h. After completion of reaction (by TLC), the reaction mixture was diluted with water and extracted with $CH_2Cl_2$ (3×10 mL). The combined organic layer was dried over $Na_2SO_4$ and concentrated under reduced pressure, crude material was purified over $SiO_2$ using $CH_2Cl_2$:MeOH as an eluent. To a stirred solution of N-oxide of Compound 5 (150 mg, 0.691 mmol) in $CH_2Cl_2$ was added benzoylisocyanate (304 mg, 2.07 mmol). The resulting reaction mixture was stirred at 55° C. for 1 h. After completion of reaction (monitored by TLC), the solvent was evaporated. The residue was re-dissolved in MeOH (5 mL), NaOMe (186 mg, 3.45 mmol) was added and refluxed for 2 h. The solvent was evaporated and the crude material was purified by flash chromatography to furnish Compound 6 as a white solid (125 mg, 83%).

Compounds 6a-6i were synthesized according to the general procedure for the synthesis of Compound 6: 3-(Methyloxy)quinolin-2-amine (Compound 6a); 3-(Ethyloxy)quinolin-2-amine (Compound 6b); 3-(Propyloxy)quinolin-2-amine (Compound 6c); 3-(Pentyloxy)quinolin-2-amine (Compound 6d); 3-(Hexyloxy)quinolin-2-amine (Compound 6e); 3-(Isopropyloxy)quinolin-2-amine (Compound 6f); 3-(Isobutyloxy)quinolin-2-amine (Compound 6g); 3-(Isopentyloxy)quinolin-2-amine (Compound 6h); and (S)-3-(2-Methylbutyloxy)quinolin-2-amine (Compound 6i).

Synthesis of 3-Azido-2-chloroquinoline (Compound 7):

To a stirred solution of (2-chloroquinolin-3-yl)boronic acid (200 mg, 0.966 mmol) in MeOH were added $CuSO_4.5H_2O$ (25 mg, 0.096 mmol) and sodium azide (75 mg, 1.159 mmol). The resulting reaction mixture was stirred at room temperature for 4 h. After completion of reaction (monitored by TLC), the solid was filtered and washed with methanol to give Compound 7 as a brown solid (170 mg, 86%), which was used for next step without purification.

Synthesis of 2-Chloroquinolin-3-amine (Compound 8):

To a stirred solution of Compound 7 (200 mg, 0.490 mmol) in EtOH (2 mL), was added Pt/C (125 mg) under nitrogen atmosphere. The reaction mixture was then stirred under H$_2$ (50 psi) for 1 h. The catalyst was removed by filtration, solvent was evaporated under reduced pressure, and the crude residue purified by flash chromatography using CH$_2$Cl$_2$:MeOH as an eluent to obtain Compound 8 as a white solid (156 mg, 86%).

Synthesis of N$^3$-Butylquinoline-2,3-diamine (Compound 9):

To a solution of Compound 8 (130 mg, 0.730 mmol) in DMF was added butyl iodide (99 µL, 0.876 mmol) under the nitrogen, the resulting mixture was stirred at 60° C. for 12 h. The solvent was evaporated under reduced pressure, diluted with water and extracted with ethyl acetate to obtain N-butyl-2-chloroquinolin-3-amine (50 mg, 0.213 mmol). The alkylated compound was dissolved in 1M ammonia solution (in methanol 2 mL). The reaction mixture was then heated to 100° C. for 24 h. The solvent was evaporated under reduced pressure, and the crude residue purified by flash chromatography using CH$_2$Cl$_2$:MeOH as an eluent to obtain Compound 9 as a white solid (15 mg, 33%).

Synthesis of 3-Bromoquinoline 1-oxide (Compound 11):

To a stirred solution of substrate Compound 10 (400 mg, 1.92 mmol) in CHCl$_3$ was added m-CPBA (1288 mg, 5.76 mmol). The resulting reaction mixture was stirred at room temperature for 4 h. After completion of reaction (monitored by TLC), the reaction mixture was diluted with water and extracted with CH$_2$Cl$_2$ (3×10 mL). The combined organic layer was dried over Na$_2$SO$_4$, concentrated under reduced pressure, and the crude material was purified by flash chromatography to get Compound 11 as white solid (360 mg, 84%).

Synthesis of 3-(Butylthio)quinolin-2-amine (Compound 12):

To a stirred solution of N-oxide of Compound 11 (89 mg, 0.381 mmol) in CH$_2$C$_2$ was added benzoylisocyanate (168 mg, 1.145 mmol). The resulting reaction mixture was stirred at 55° C. for 1 h. After completion of reaction (monitored by TLC), the solvent was evaporated. The residue was re-dissolved in MeOH (5 mL), NaOMe (102 mg, 1.90 mmol) was added and refluxed for 2 h. The solvent was evaporated and the crude material was purified by flash chromatography to furnish Compound 12 as a white solid (75 mg, 85%).

General Procedure for the Synthesis of 3-Butylquinoline 1-oxide (Compound 13a):

To a stirred solution of substrate Compound 11 (100 mg, 0.446 mmol) in 1,4-dioxane was added butylboronic acid (91 mg, 0.892 mmol), Pd(PPh$_3$)$_4$ (25 mg, 0.0228 mmol) and K$_2$CO$_3$ (184 mg, 1.33 mmol). The resulting reaction mixture was stirred at 90° C. under nitrogen atmosphere for 12 h. After completion of reaction (monitored by TLC), the reaction mixture was diluted with water and extracted with ethyl acetate (3×10 mL). The combined organic layer was dried over Na$_2$SO$_4$ and concentrated under reduced pressure, crude material was purified by flash chromatography using CH$_2$Cl$_2$:MeOH as an eluent to obtain Compound 13a as a white solid (72 mg, 80%).

Compounds 13b-13f were synthesized according to the general procedure for the synthesis of Compound 13a: 3-Pentylquinoline 1-oxide (Compound 13b); 3-Hexylquinoline 1-oxide (Compound 13c); (E)-3-(Pent-1-en-1-yl)quinoline 1-oxide (Compound 13d); 3-(Pent-4-en-1-yl)quinoline 1-oxide (Compound 13e); and 3-(Pent-1-yn-1-yl)quinoline 1-oxide (Compound 13f).

General Procedure for the Synthesis of 3-Butylquinolin-2-amine (Compound 14a):

To a stirred solution of N-oxide of Compound 13a (50 mg, 0.248 mmol) in CH$_2$Cl$_2$ was added benzoylisocyanate (109 mg, 0.741 mmol). The resulting reaction mixture was stirred at 55° C. for 1 h. After completion of reaction (monitored by TLC), the solvent was evaporated. The residue was re-dissolved in MeOH (5 mL), NaOMe (67 mg, 1.24 mmol) was added and refluxed for 2 h. The solvent was evaporated and the crude material was purified by flash chromatography using CH$_2$Cl$_2$:MeOH as an eluent to furnish Compound 14a as a white solid (40 mg, 81%).

Compounds 14b-14f were synthesized according to the general procedure for the synthesis of Compound 14a: 3-Pentylquinolin-2-amine (Compound 14b); 3-Hexylquinolin-2-amine (Compound 14c); (E)-3-(Pent-1-en-1-yl)quinolin-2-amine (Compound 14d); 3-(Pent-4-en-1-yl)quinolin-2-amine (Compound 14e); and 3-(Pent-1-yn-1-yl)quinolin-2-amine (Compound 14f).

Synthesis of 4-Chloro-3-iodoquinoline (Compound 16):

Substrate 3-iodoquinolin-4-ol Compound 15 (1000 mg, 3.69 mmol) was dissolved in 25 mL of POCl$_3$. The resulting reaction mixture was stirred at 100° C. for 2 h. After completion of reaction (monitored by TLC), the solvent was evaporated under reduced pressure and added ice cold water. The solid was filtered and dried under the vacuum to get Compound 16 as a white solid (900 mg, 85%).

Synthesis of 4-Chloro-3-(pent-1-yn-1-yl)quinoline (Compound 17):

To a stirred solution of 4-chloro-3-iodoquinoline Compound 16 (500 mg, 1.730 mmol) in acetonitrile:triethylamine (3:1) were added the pent-1-yne (341 µL, 3.46 mmol), Pd(PPh$_3$)$_4$ (92.4 mg, 0.08 mmol) and CuI (13.14 mg, 0.069 mmol). The resulting reaction mixture was stirred at 70° C. under nitrogen atmosphere for 12 h. After completion of reaction (monitored by TLC), the reaction mixture was diluted with water and extracted with ethylacetate (3×10 mL). The combined organic layer was dried over Na$_2$SO$_4$ and concentrated under reduced pressure, crude material was purified by flash chromatography using CH$_2$Cl$_2$:MeOH as an eluent to obtain Compound 17 as a white solid (325 mg, 82%).

General Procedure for the Synthesis of 4-Methyl-3-(pent-1-yn-1-yl)quinoline (Compound 18a):

To a stirred solution of substrate Compound 17 (150 mg, 0.655 mmol) in 1,4-dioxane were added the methylboronic acid (78 mg, 1.31 mmol), Pd(PPh$_3$)$_4$ (37 mg, 0.032 mmol) and K$_2$CO$_3$ (271 mg, 1.965 mmol). The resulting reaction mixture was stirred at 90° C. under nitrogen atmosphere for 12 h. After completion of reaction (monitored by TLC), the reaction mixture was diluted with water and extracted with ethyl acetate (3×10 mL). The combined organic layer was dried over Na$_2$SO$_4$ and concentrated under reduced pressure, crude material was purified by flash chromatography using CH$_2$Cl$_2$:MeOH as an eluent to obtain Compound 18a as a colorless liquid (100 mg, 73%). Compounds 18b-18c were synthesized according to the general procedure for the synthesis of Compound 18a.

General Procedure for the Synthesis of 4-Methyl-3-pentylquinoline (Compound 19a):

To a stirred solution of Compound 18a (125 mg, 0.586 mmol) in EtOH (2 mL), was added Pt/C (125 mg) under nitrogen atmosphere. The reaction mixture was then stirred under H$_2$ (50 psi) for 1 h. The catalyst was removed by filtration, solvent was evaporated under reduced pressure, and the crude residue purified by flash chromatography using CH$_2$Cl$_2$:MeOH as an eluent to obtain Compound 19a as a white solid (86 mg, 68%). Compounds 19b-19c were synthesized according to the general procedure for the synthesis of Compound 19a.

General Procedure for the Synthesis of 4-Methyl-3-pentylquinoline 1-oxide (Compound 20a):

To a stirred solution of substrate Compound 19a (100 mg, 0.469 mmol) in $CHCl_3$ was added m-CPBA (243 mg, 1.408 mmol). The resulting reaction mixture was stirred at room temperature for 4 h. After completion of reaction (monitored by TLC), the reaction mixture was diluted with water and extracted with $CH_2Cl_2$ (3×10 mL). The combined organic layer was dried over $Na_2SO_4$, concentrated under reduced pressure, and the crude material was purified by flash chromatography using $CH_2Cl_2$:MeOH as an eluent to obtain Compound 20a as white solid (91 mg, 85%).

Compounds 20b-20c were synthesized according to the general procedure for the synthesis of Compound 20a: 4-Ethyl-3-pentylquinoline 1-oxide (Compound 20b); and 4-Isopentyl-3-pentylquinoline 1-oxide (Compound 20c).

General Procedure for the Synthesis of 4-Methyl-3-pentylquinolin-2-amine (Compound 21a):

To a stirred solution of N-oxide of Compound 20a (50 mg, 0.218 mmol) in $CH_2Cl_2$ was added benzoylisocyanate (96 mg, 0.653 mmol). The resulting reaction mixture was stirred at 55° C. for 1 h. After completion of reaction (monitored by TLC), the solvent was evaporated. The residue was re-dissolved in MeOH (5 mL), NaOMe (105 mg, 1.94 mmol) was added and refluxed for 2 h. The solvent was evaporated and the crude material was purified by flash chromatography using $CH_2Cl_2$:MeOH as an eluent to furnish Compound 21a as a white solid (35 mg, 70%).

Compounds 21b-21c were synthesized according to the general procedure for the synthesis of Compound 21a: 4-Ethyl-3-pentylquinolin-2-amine (Compound 21b); and 4-Isopentyl-3-pentylquinolin-2-amine (Compound 21c).

General Procedure for the Synthesis of 4-(Butyloxy)quinoline (Compound 23a):

To a stirred solution of quinolin-4-ol Compound 22 (472 mg, 3.25 mmol) in DMSO were added $K_2CO_3$ (898 mg, 6.50 mmol) and butyliodide (555 ILL, 4.87 mmol). The resulting reaction mixture was stirred at 80° C. for 4 h. After completion of reaction (monitored by TLC), the reaction mixture was diluted with water and extracted with diethyl ether (3×15 mL). The combined organic layer was dried over $Na_2SO_4$, concentrated under reduced pressure, and the crude material was purified by flash chromatography to obtain Compound 23a as white solid (350 mg, 84%). Compound 23b (4-(Pentyloxy)quinoline) was synthesized according to the general procedure for the synthesis of Compound 23a.

General Procedure for the Synthesis of 4-(Butyloxy)quinolin-2-amine (Compound 24a):

To a stirred solution of substrate Compound 23a (238 mg, 1.18 mmol) in $CHCl_3$ was added m-CPBA (612 mg, 3.55 mmol), the resulting reaction mixture was stirred at r.t. for 4 h. After completion of reaction (by TLC), the reaction mixture was diluted with water and extracted with $CH_2Cl_2$ (3×10 mL). The combined organic layer was dried over $Na_2SO_4$ and concentrated under reduced pressure, crude material was purified over $SiO_2$ using $CH_2Cl_2$:MeOH as an eluent. To a stirred solution of N-oxide of Compound 23a (151 mg, 0.697 mmol) in $CH_2Cl_2$ was added benzoylisocyanate (304 mg, 2.07 mmol). The resulting reaction mixture was stirred at 55° C. for 1 h. After completion of reaction (monitored by TLC), the solvent was evaporated. The residue was re-dissolved in MeOH (5 mL), NaOMe (186 mg, 3.45 mmol) was added and refluxed for 2 h. The solvent was evaporated and the crude material was purified by flash chromatography to furnish Compound 24a as a white solid (78 mg, 78%). Compound 24b (4-(Pentyloxy)quinolin-2-amine) was synthesized according to the procedure for the synthesis of Compound 24a.

General Procedure for the Synthesis of 4-Butylquinoline (Compound 26a):

To a stirred solution of substrate Compound 25 (187 mg, 1.14 mmol) in 1,4-dioxane were added the butylboronic acid (234 mg, 2.28 mmol), $Pd(PPh_3)_4$ (37 mg, 0.032 mmol) and $K_2CO_3$ (472 mg, 3.42 mmol). The resulting reaction mixture was stirred at 90° C. under nitrogen atmosphere for 12 h. After completion of reaction (monitored by TLC), the reaction mixture was diluted with water and extracted with ethyl acetate (3×10 mL). The combined organic layer was dried over $Na_2SO_4$ and concentrated under reduced pressure, crude material was purified by flash chromatography using $CH_2Cl_2$:MeOH as an eluent to obtain Compound 26a as a colorless liquid (100 mg, 73%). Colorless liquid (170 mg, 80%). Compound 26b (4-Pentylquinoline) was synthesized according to the procedure for the synthesis of 26a.

General Procedure for the Synthesis of 4-Butylquinolin-2-amine (Compound 27a):

To a stirred solution of substrate Compound 26a (173 mg, 0.935 mmol) in $CHCl_3$ was added m-CPBA (483 mg, 2.80 mmol), the resulting reaction mixture was stirred at r.t. for 4 h. After completion of reaction (by TLC), the reaction mixture was diluted with water and extracted with $CH_2Cl_2$ (3×10 mL). The combined organic layer was dried over $Na_2SO_4$ and concentrated under reduced pressure, crude material was purified over $SiO_2$ using $CH_2Cl_2$:MeOH as an eluent. To a stirred solution of N-oxide of Compound 26a (125 mg, 0.621 mmol) in $CH_2Cl_2$ was added benzoylisocyanate (273 mg, 1.86 mmol). The resulting reaction mixture was stirred at 55° C. for 1 h. After completion of reaction (monitored by TLC), the solvent was evaporated. The residue was re-dissolved in MeOH (5 mL), NaOMe (168 mg, 3.10 mmol) was added and refluxed for 2 h. The solvent was evaporated and the crude material was purified by flash chromatography to furnish Compound 27a as a white solid (100 mg, 80%). Compound 27b (4-Pentylquinolin-2-amine) was synthesized according to the procedure for the synthesis of 27a.

TABLE 1

$EC_{50}$ values of compounds in human TLR8-specific reporter gene assays

| Compound # | Structure | Agonistic Activity $EC_{50}$ ($\mu M$) TLR8 |
|---|---|---|
| 6 | quinoline with $NH_2$ and O-butyl substituents | 2.18 |
| 9 | quinoline with $NH_2$ and NH-butyl substituents | 4.28 |
| 12 | quinoline with $NH_2$ and S-butyl substituents | 4.16 |

TABLE 1-continued
EC$_{50}$ values of compounds in human TLR8-specific reporter gene assays
| Compound # | Structure | Agonistic Activity EC$_{50}$ (μM) TLR8 |
|---|---|---|
| 14a | 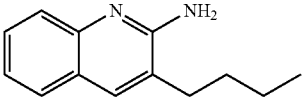 | 0.41 |
| 14b | 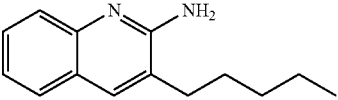 [SMILES: CCCCCc1cc2ccccc2nc1N] | 0.2 |
| 14c | 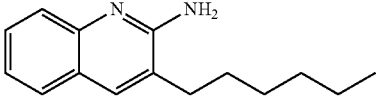 [SMILES: CCCCCCc1cc2ccccc2nc1N] | Inactive |
| 14d | 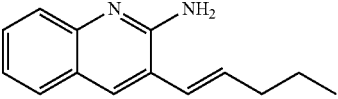 [SMILES: CCC/C=C/c1cc2ccccc2nc1N] | 2.67 |
| 14e | 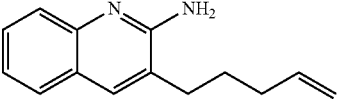 [SMILES: C=CCCCc1cc2ccccc2nc1N] | 0.49 |
| 14f | 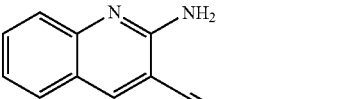 | 12.96 |
| 6a | 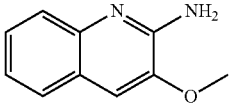 | 100 |
| 6b | 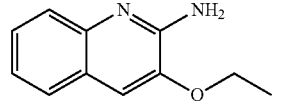 | 100 |
| 6c | 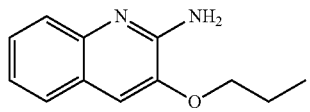 | 5 |
| 6d | 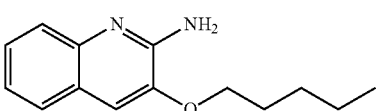 | 7 |
| 6e | 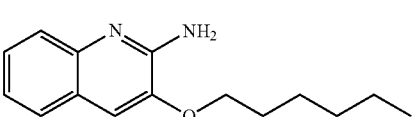 | 50 |
| 6f | 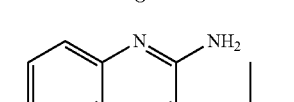 | 100 |
| 6g | 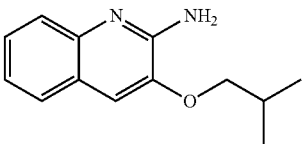 [SMILES: CC(C)COc1cc2ccccc2nc1N] | 50 |
| 6h | 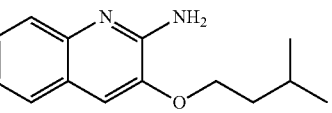 | 50 |
| 6l | 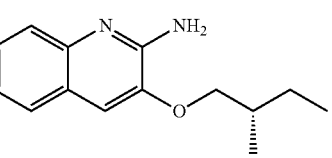 | 10 |
| 21a | 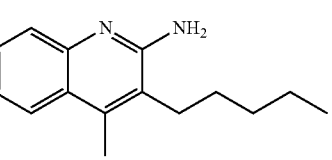 | Inactive[a] |
| 21b | 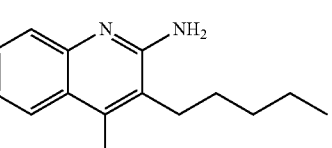 | Inactive |
| 21c | 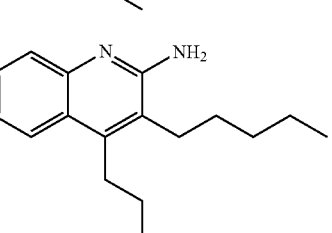 | Inactive |
| 24a | 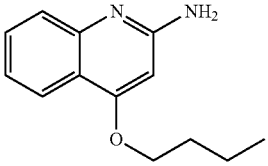 [SMILES: CCCCOc1cc(N)nc2ccccc12] | Inactive |
| 24b | 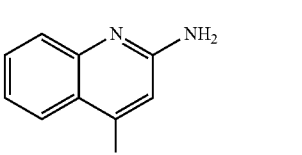 | Inactive |

TABLE 1-continued

EC$_{50}$ values of compounds in human TLR8-specific reporter gene assays

| Compound # | Structure | Agonistic Activity EC$_{50}$ (μM) TLR8 |
|---|---|---|
| 27a | (structure: 2-amino-4-butylquinoline) | Inactive |
| 27b | (structure: 2-amino-4-pentylquinoline) | Inactive |

Synthesis of 4-iodoquinolin-3-ol (Compound A5):

In an oven dried round bottom flask equipped with a stirring bar was placed 3-hydroxy quinoline (1.0 g, 6.89 mmol) in 2N NaOH (20 mL). To this mixture a solution of iodine (8.27 mmol) in 20% of aqueous potassium iodide (20 mL) was added drop-wise and stirred for 3 h at room temperature. The mixture was then acidified with acetic acid, and the precipitate was filtered and washed with water. After drying under vacuum, 1.50 g of 5 was obtained, which was used without purification.

General Procedure for Sonogashira Reaction:

To a stirred solution of 4-iodoquinolin-3-ol in acetonitrile:triethylamine (2:1) were added the appropriate alkyne (0.553 mmol), Pd(PPh$_3$)$_4$ (0.018 mmol) and CuI (0.018 mmol). The resulting reaction mixture was stirred at 70° C. under nitrogen atmosphere for 12 h. After completion of reaction (monitored by TLC), the reaction mixture was diluted with water and extracted with ethylacetate (3×10 mL). The combined organic layer was dried over Na$_2$SO$_4$ and concentrated under reduced pressure, crude material was purified by flash chromatography using CH$_2$Cl$_2$:MeOH as an eluent.

The following are selected compounds: 2-propylfuro[2,3-c]quinoline (Compound A6c); 2-butylfuro[2,3-c]quinoline (Compound A6d); 2-pentylfuro[2,3-c]quinoline (Compound A6e); 2-hexylfuro[2,3-c]quinoline (Compound A6f); 2-isobutylfuro[2,3-c]quinoline (Compound A6g); 2-(tert-butyl)furo[2,3-c]quinoline (Compound A6h); 2-isopentylfuro[2,3-c]quinoline (Compound A6i); 2-cyclopropylfuro[2,3-c]quinoline (Compound A6j); 2-cyclopentylfuro[2,3-c]quinoline (Compound A6k); 2-(cyclopentylmethyl)furo[2,3-c]quinoline (Compound A6l); 2-(cyclohexylmethyl)furo[2,3-c]quinoline (Compound A6m); 2-phenylfuro[2,3-c]quinoline (Compound A6n); furo[2,3-c]quinolin-2-ylmethanol (Compound A6p); 2-(furo[2,3-c]quinolin-2-yl)ethanol (Compound A6q); 4-(furo[2,3-c]quinolin-2-yl)butan-1-ol (Compound A6s); 2-(furo[2,3-c]quinolin-2-yl)propan-2-ol (Compound A6t); 1-(furo[2,3-c]quinolin-2-yl)propan-2-ol (Compound A6v); 2-(2-ethoxyethyl)furo[2,3-c]quinoline (Compound A6w); 2-(furo[2,3-c]quinolin-2-ylmethyl)isoindoline-1,3-dione (Compound A6x); and 2-(2-(furo[2,3-c]quinolin-2-yl)ethyl)isoindoline-1,3-dione (Compound A6y).

General Procedure for N-Oxidation:

To a stirred solution of substrate (0.53 mmol) in CHCl$_3$ was added m-CPBA (1.06 mmol). The resulting reaction mixture was stirred at room temperature for 4 h. After completion of reaction (monitored by TLC), the reaction mixture was diluted with water and extracted with CH$_2$Cl$_2$ (3×10 mL). The combined organic layer was dried over Na$_2$SO$_4$, concentrated under reduced pressure, and the crude material was purified by flash chromatography.

The following are selected compounds: 2-methylfuro[2,3-c]quinoline 5-oxide (Compound A7b); 2-propylfuro[2,3-c]quinoline 5-oxide (Compound A7c); 2-butylfuro[2,3-c]quinoline 5-oxide (Compound A7d); 2-pentylfuro[2,3-c]quinoline 5-oxide (Compound A7e); 2-hexylfuro[2,3-c]quinoline 5-oxide (Compound A7f); 2-isobutylfuro[2,3-c]quinoline 5-oxide (Compound A7g); 2-(tert-butyl)furo[2,3-c]quinoline 5-oxide (Compound A7h); 2-isopentylfuro[2,3-c]quinoline 5-oxide (Compound A7i); 2-cyclopropylfuro[2,3-c]quinoline 5-oxide (Compound A7j); 2-cyclopentylfuro[2,3-c]quinoline 5-oxide (Compound A7k); 2-(cyclopentylmethyl)furo[2,3-c]quinoline 5-oxide (Compound A7l); 2-(cyclohexylmethyl)furo[2,3-c]quinoline 5-oxide (Compound A7m); 2-phenylfuro[2,3-c]quinoline 5-oxide (Compound A7n); 2-benzylfuro[2,3-c]quinoline 5-oxide (Compound A7o); 2-(hydroxymethyl)furo[2,3-c]quinoline 5-oxide (Compound A7p); 2-(2-hydroxyethyl)furo[2,3-c]quinoline 5-oxide (Compound A7q); 2-(3-hydroxypropyl)furo[2,3-c]quinoline 5-oxide (Compound A7r); 2-(4-hydroxybutyl)furo[2,3-c]quinoline 5-oxide (Compound A7s); 2-(2-hydroxypropan-2-yl)furo[2,3-c]quinoline 5-oxide (Compound A7t); 2-(1-hydroxy-3-methylbutyl)furo[2,3-c]quinoline 5-oxide (Compound A7u);–(2-hydroxypropyl)furo[2,3-c]quinoline 5-oxide (Compound A7v); 2-(2-ethoxyethyl)furo[2,3-c]quinoline 5-oxide (Compound A7w); 2-((1,3-dioxoisoindolin-2-yl)methyl)furo[2,3-c]quinoline 5-oxide (Compound A7x); and 2-(2-(1,3-dioxoisoindolin-2-yl)ethyl)furo[2,3-c]quinoline 5-oxide (Compound A7y).

General Procedure for Installation of the 4-Amino Group:

To a stirred solution of N-oxide (0.414 mmol) in CH$_2$Cl$_2$ was added benzoylisocyanate (1.24 mmol). The resulting reaction mixture was stirred at 55° C. for 2 h. After completion of reaction (monitored by TLC), the solvent was evaporated. The residue was re-dissolved in MeOH (4 mL), and NaOMe (2.07 mmole) was added and refluxed for 4 h. The solvent was evaporated and the crude material was purified by flash chromatography using CH$_2$Cl$_2$:MeOH as an eluent. For compounds A8x and A8y, after reaction with benzoylisocyanate (1st step), the solvent was evaporated, ethylenediamine (2 mL) was added and stirred at 70° C. for 12 h.

The following are selected compounds: furo[2,3-c]quinolin-4-amine (Compound A8a); 2-methylfuro[2,3-c]quinolin-4-amine (Compound A8b); 2-propylfuro[2,3-c]quinolin-4-amine (Compound A8c); 2-butylfuro[2,3-c]quinolin-4-amine (Compound A8d); 2-pentylfuro[2,3-c]quinolin-4-amine (Compound A8e); 2-hexylfuro[2,3-c]quinolin-4-amine (Compound A8f); 2-isobutylfuro[2,3-c]quinolin-4-amine (Compound A8g); 2-(tert-butyl)furo[2,3-c]quinolin-4-amine (Compound A8h); 2-isopentylfuro[2,3-c]quinolin-4-amine (Compound A8i); 2-cyclopropylfuro[2,3-c]quinolin-4-amine (Compound A8j); 2-cyclopentylfuro[2,3-c]quinolin-4-amine (Compound A8k); 2-(cyclopentylmethyl)furo[2,3-c]quinolin-4-amine (Compound A8l); 2-(cyclohexylmethyl)furo[2,3-c]quinolin-4-amine (Compound A8m); 2-phenylfuro[2,3-c]quinolin-4-amine (Compound A8n); 2-benzylfuro[2,3-c]quinolin-4-amine (Compound A8o); (4-aminofuro[2,3-c]quinolin-2-yl)methanol (Compound A8p); 2-(4-aminofuro[2,3-c]quinolin- 2-yl)ethanol (Compound A8q); 3-(4-aminofuro[2,3-c]quinolin-2-yl)propan-1-ol (Compound A8r); 4-(4-aminofuro[2,3-c]quinolin-2-yl)butan-1-ol (Compound A8s); 2-(4-aminofuro[2,3-c]quinolin-2-yl)propan-2-ol (Compound A8t); 1-(4-aminofuro[2,3-c]quinolin-2-yl)-3-methylbutan-1-ol (Compound A8u); 1-(4-aminofuro[2,3-c]quinolin-2-yl)propan-2-ol (Compound A8v); 2-(2-ethoxyethyl)furo[2,3-c]quinolin-4-amine (Compound A8w); 2-(aminomethyl)furo[2,3-c]quinolin-4-amine (Compound A8x); 2-(2-aminoethyl)furo[2,3-c]quinolin-4-amine (Compound A8y)

Compound A10 (3-iodoquinolin-4-ol) was synthesized similarly as Compound A5.

Compounds A11a (2-propylfuro[3,2-c]quinoline), A11b (2-butylfuro[3,2-c]quinoline), and A11c (2-phenylfuro[3,2-c]quinoline) were synthesized similarly as Compound A6c.

Compounds A12a (2-propylfuro[3,2-c]quinoline 5-oxide), A12b (2-butylfuro[3,2-c]quinoline 5-oxide), and A12c (2-phenylfuro[3,2-c]quinoline 5-oxide) were synthesized similarly as Compound A7b.

Compounds A13a (2-propylfuro[3,2-c]quinolin-4-amine), A13b (2-butylfuro[3,2-c]quinolin-4-amine), and A13c (2-phenylfuro[3,2-c]quinolin-4-amine) were synthesized similarly as Compound A8a.

Compound A15 (4-iodoisoquinolin-3-ol) was synthesized similarly as Compound A5.

Compound A16 (2-butylfuro[2,3-c]isoquinoline) was synthesized similarly as Compound A6c.

Compound A17 (2-butylfuro[2,3-c]isoquinoline 4-oxide) was synthesized similarly as Compound A7b.

Compound A18 (2-butylfuro[2,3-c]isoquinolin-5-amine) was synthesized similarly as Compound A8a 1-bromo-2-butylfuro[2,3-c]quinoline (Compound A19):

To a stirred solution of 2-butylfuro[2,3-c]quinoline Compound A7d (100 mg, 0.44 mmol) in $CH_2Cl_2$ was added bromine (80 μL, 1.55 mmol) and stirred at room temperature for 6 h. After completion of reaction (monitored by TLC), the solvent was evaporated, the crude material was purified by flash chromatography using $CH_2Cl_2$:MeOH to furnish Compound A19 as yellow solid (50 mg, 75%).

Compound A21 (1-bromo-2-butylfuro[2,3-c]quinolin-4-amine) was synthesized similarly as Compound A8a.

1-benzyl-2-butylfuro[2,3-c]quinoline (Compound A22):

To a stirred solution of Compound A19 (50 mg, 0.164 mmol) in 1,4-dioxane were added 2-benzyl-4,4,5,5-tetramethyl-1,3,2-dioxaborolane (54 mg, 0.246 mmol), Pd(dppf)$Cl_2$ (8 mg, 0.009 mmol), $Cs_2CO_3$ (160 mg, 0.492 mmol) and 0.1 ml of water. The resulting reaction mixture was stirred at 70° C. under nitrogen atmosphere for 12 h. After completion of reaction (monitored by TLC), the reaction mixture was diluted with water and extracted with ethylacetate (3×10 mL). The combined organic layer was dried over $Na_2SO_4$ and concentrated under reduced pressure, crude material was purified by flash chromatography using $CH_2Cl_2$:MeOH as an eluent to obtain Compound A22 (24 mg, 92%).

Compound A24 (1-benzyl-2-butylfuro[2,3-c]quinolin-4-amine) was synthesized similarly as Compound A8a.

Compounds A27a (2-propylfuro[2,3-c]pyridine 6-oxide) and A27b (2-butylfuro[2,3-c]pyridine 6-oxide) were synthesized similarly as Compound A7b.

Compounds A28a (2-propylfuro[2,3-c]pyridin-7-amine) and A28b (2-butylfuro[2,3-c]pyridin-7-amine) was synthesized similarly as Compound A8a.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself. In some embodiments, compounds described herein can be used to treat disorders, or inhibit disorders by being an adjuvant of a vaccine.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition. Here, the compounds can be used as adjuvants in a vaccines, and vaccines are used to inhibit prevent disease, and thereby the compounds can be used to prevent diseases. However, it can be clear that the compounds are adjuvants of vaccines and thereby they can be used in processes for inhibiting a disease, such as inhibiting contraction of the disease or disease state.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. The therapeutically effective amount can be as an adjuvant.

The term "$IC_{50}$" or "$EC_{50}$" refers an amount, concentration, or dosage of a compound that is required for 50% inhibition of a maximal response in an assay that measures such response.

The term "$CC_{50}$" refers an amount, concentration, or dosage of a compound that results in 50% reduction of the viability of a host. In certain embodiments, the $CC_{50}$ of a compound is the amount, concentration, or dosage of the compound that is required to reduce the viability of cells treated with the compound by 50%, in comparison with cells untreated with the compound.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein. The vaccine agent or the compound adjuvant can be an active ingredient or substance.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease. The vaccine agent or the compound adjuvant can be a therapeutic agent or drug as they are used in inducing resistance of a disease.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). The R groups can include an alkyl group.

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). The R groups can include an alkylene group. The term alkyl can also generically refer to alkylenes when both ends have radicals.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—. In certain embodiments, heteroalkylene may also be optionally substituted with one or more substituents Q as described herein. The R groups can include a heteroalkylene group.

The term "alkenyl" refers to a linear or branched monovalent hydrocarbon radical, which contains one or more, in one embodiment, one to five, in another embodiment, one, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. The R groups can include an alkenyl group. The term alkenyl can also generically refer to alkenylenes when both ends have radicals.

The term "alkenylene" refers to a linear or branched divalent hydrocarbon radical, which contains one or more, in one embodiment, one to five, in another embodiment, one, carbon-carbon double bond(s). The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene. The R groups can include an alkenylene group.

The term "heteroalkenylene" refers to a linear or branched divalent hydrocarbon radical, which contains one or more, in one embodiment, one to five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—. The R groups can include a heteroalkenylene group.

The term "alkynyl" refers to a linear or branched monovalent hydrocarbon radical, which contains one or more, in one embodiment, one to five, in another embodiment, one, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl). The R groups can include an alkynyl group. The term alkynyl can also generically refer to alkynylenes when two ends have radicals.

The term "alkynylene" refers to a linear or branched divalent hydrocarbon radical, which contains one or more, in one embodiment, one to five, in another embodiment, one, carbon-carbon triple bond(s). The alkynylene may be optionally substituted with one or more substituents Q as described herein. For example, $C_{2-6}$ alkynylene refers to a linear unsaturated divalent hydrocarbon radical of 2 to 6 carbon atoms or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene, propynylene (including all isomeric forms, e.g., 1-propynylene and prop-argylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene). The R groups can include an alkynylene group.

The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl. The R groups can include a cycloalkyl group. The term cycloalkyl can also generically refer to cycloalkylenes when two ends have radicals.

The term "cycloalkylene" refers to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene. The R groups can include a cycloalkyl group.

The term "aryl" refers to a monovalent monocyclic aromatic group and/or monovalent polycyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein. The R groups can include an aryl group. The term aryl can also generically refer to arylenes when two ends have radicals.

The term "arylene" refers to a divalent monocyclic aromatic group and/or divalent polycyclic aromatic group that contain at least one aromatic carbon ring. In certain embodiments, the arylene has from 6 to 20 ($C_{6-20}$), from 6 to 15 ($C_{6-15}$), or from 6 to 10 ($C_{6-10}$) ring atoms.

Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydronaphthylene (tetralinylene). In certain embodiments, arylene may be optionally substituted with one or more substituents Q as described herein. The R groups can include an arylene group.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents Q as described herein. The R groups can include an aralkyl or arylalkyl group. The term arylalkyl can also generically refer to arylalkylenes when two ends have radicals.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein. The R groups can include a heteroaryl group. The term heteroaryl can also generically refer to heteroarylenes when two ends have radicals.

The term "heteroarylene" refers to a divalent monocyclic aromatic group or divalent polycyclic aromatic group that contain at least one aromatic ring, wherein at least one aromatic ring contains one or more heteroatoms independently selected from O, S, and N in the ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein. The R groups can include a heteroarylene group.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein. The R groups can include a heterocyclic group. The term heterocyclic can also generically refer to heterocyclenes when both ends have radicals.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3, 5-trithianylene. In certain embodiments, heterocyclic may also be optionally substituted with one or more substituents Q as described herein. The R groups can include a heterocyclylene group.

The term "halogen", "halide" or "halo" refers to fluorine, chlorine, bromine, and/or iodine. The R groups can include a halogen group.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, or heterocyclylene group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q; and (b) oxo (=O), halo, cyano (—CN), nitro (—$NO_2$), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(N$R^a$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all R groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N) nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I) iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium. The R groups can include isotopic variants.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a mixture of diastereomers, or an isotopic variant thereof; or a pharmaceutically acceptable salt, solvate, or prodrug thereof" has the same meaning as the phrase "a single enantiomer, a racemic mixture, a mixture of diastereomers, or an isotopic variant of the compound referenced therein; or a pharmaceutically acceptable salt, solvate, or prodrug of the compound referenced therein, or a single enantiomer, a racemic mixture, a mixture of diastereomers, or an isotopic variant of the compound referenced therein."

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A pharmaceutical vaccine composition comprising:
a vaccine agent;
an adjuvant for the vaccine agent; and
a pharmaceutically acceptable carrier,
wherein the adjuvant comprises a compound comprising:
a structure of Formula 4 or 4A, or salt, stereoisomer, tautomer, polymorph, solvate, or combination thereof:

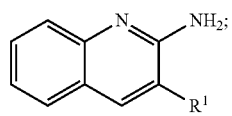

Formula 4

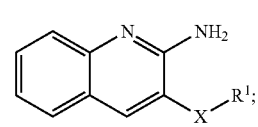

Formula 4A wherein:

X is S, O, or NH; and $R^1$ is selected from $C_1$-$C_{24}$ alkyl, $C_2$-$C_{24}$ alkenyl, $C_2$-$C_{24}$ alkynyl, and combinations thereof;
wherein $R^1$ is optionally substituted by a substituent Q, which substituent Q is selected from $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy and combinations thereof; and
wherein the structure is a toll-like receptor 8 agonist.

2. The pharmaceutical vaccine composition of claim 1, wherein $R^1$ is one of methyl, ethyl, propyl, isopropyl, $C_4H_9$, $C_5H_{11}$, pent-1-en-1-yl, pent-4-en-1-yl, or pent-1-yn-1-yl; or when Formula 4, $R^1$ is methoxy, propoxy, butoxy, pentoxy, hexoxy, isopropyloxy, isobutyloxy, isopentyloxy, or 2-methylbutoxy.

3. The pharmaceutical vaccine composition of claim 2, wherein X is O.

4. The pharmaceutical vaccine composition of claim 1, wherein the compound is selected from one of the following structures:

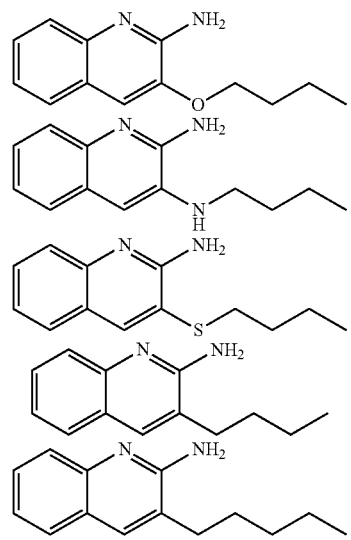

-continued

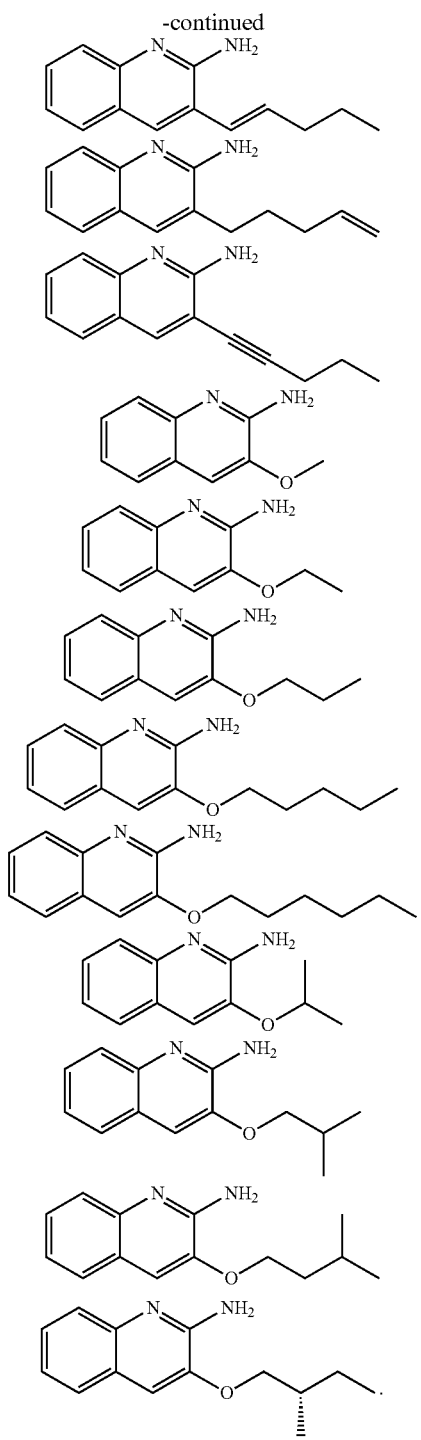

5. The pharmaceutical vaccine composition of claim 1, wherein the compound is Compound 14b:

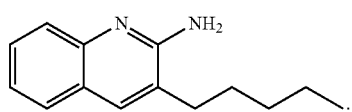

6. The pharmaceutical vaccine composition of claim 1, wherein the compound includes:

X is S, O, or NH; and $R^1$ is selected from isopropyl, $C_4$-$C_{24}$ alkyl, $C_2$-$C_{24}$ alkenyl, $C_2$-$C_{24}$ alkynyl, and combinations thereof.

7. The pharmaceutical vaccine composition of claim 1, wherein the composition is configured for oral administration, parenteral administration, intravenous administration, topical administration, or subcutaneous administration.

8. The pharmaceutical vaccine composition of claim 1, wherein the compound is present in an amount sufficient for agonizing a Toll-Like Receptor 8 (TLR8).

9. The pharmaceutical vaccine composition of claim 6, wherein $R^1$ is one of isopropyl, $C_4H_9$, $C_5H_{11}$, pent-1-en-1-yl, pent-4-en-1-yl, or pent-1-yn-1-yl; or when Formula 4, $R^1$ is butoxy, pentoxy, hexoxy, isopropyloxy, isobutyloxy, isopentyloxy, or 2-methylbutoxy.

10. The pharmaceutical vaccine composition of claim 6, wherein the compound is selected from one of the following structures:

-continued

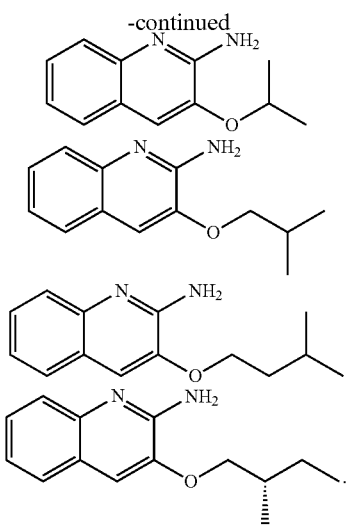

11. The pharmaceutical vaccine composition of claim 1, wherein the compound is one of the following structures:

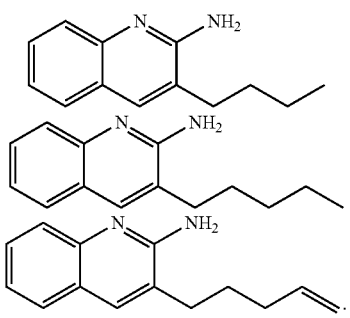

12. The pharmaceutical vaccine composition of claim 1, wherein the compound includes:

the structure of Formula 4, or salt, stereoisomer, tautomer, polymorph, solvate, or combination thereof.

13. The pharmaceutical vaccine composition of claim 1, wherein the compound includes:

the structure of Formula 4A, or salt, stereoisomer, tautomer, polymorph, solvate, or combination thereof.

14. The pharmaceutical vaccine composition of claim 1, wherein the compound includes a structure of one of the following:

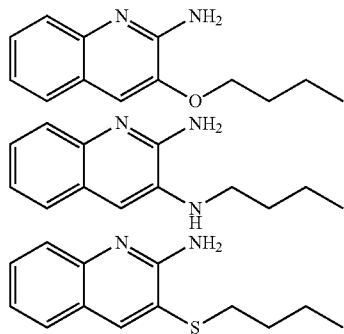

-continued

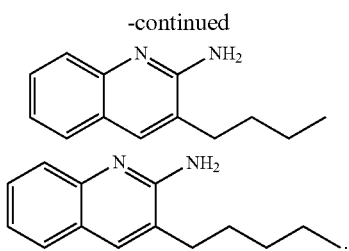

15. The pharmaceutical vaccine composition of claim 1, wherein the compound includes a structure of one of the following:

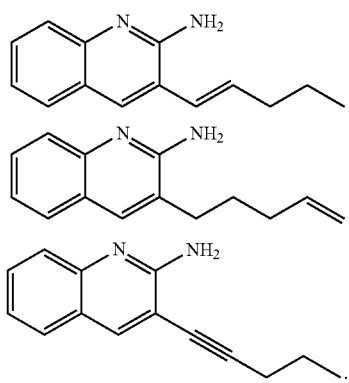

16. The pharmaceutical vaccine composition of claim 1, wherein the compound includes a structure of one of the following:

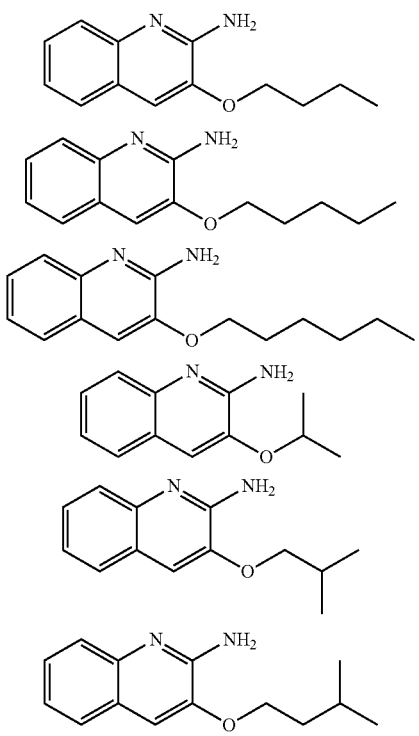

-continued
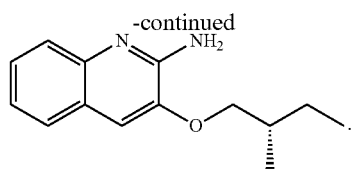
* * * * *

UNITED STATES PATENT AND TRADEMARK OFFICE
CERTIFICATE OF CORRECTION

| | |
|---|---|
| PATENT NO. | : 10,654,807 B2 |
| APPLICATION NO. | : 15/106488 |
| DATED | : May 19, 2020 |
| INVENTOR(S) | : Sunil Abraham David et al. |

It is certified that error appears in the above-identified patent and that said Letters Patent is hereby corrected as shown below:

On the Title Page

Item (72), please delete "Sunil Abraham David, St. Paul, MS (US)" and insert --Sunil Abraham David, St. Paul, MN (US)-- therefor Signed and Sealed this
First Day of October, 2024

Katherine Kelly Vidal
*Director of the United States Patent and Trademark Office*